United States Patent
Sumitran-Holgersson et al.

(10) Patent No.: US 12,090,253 B2
(45) Date of Patent: Sep. 17, 2024

(54) BIOENGINEERED ALLOGENEIC BLOOD VESSEL

(71) Applicant: VeriGraft AB, Gothenburg (SE)

(72) Inventors: Suchitra Sumitran-Holgersson, Gothenburg (SE); Michael Olausson, Gothenburg (SE)

(73) Assignee: VeriGraft AB, Gothenburg (SE)

( * ) Notice: Subject to any disclaimer, the term of this patent is extended or adjusted under 35 U.S.C. 154(b) by 328 days.

(21) Appl. No.: 16/728,138

(22) Filed: Dec. 27, 2019

(65) Prior Publication Data

US 2020/0147272 A1     May 14, 2020

Related U.S. Application Data

(60) Continuation of application No. 15/481,862, filed on Apr. 7, 2017, now Pat. No. 10,517,996, which is a division of application No. 15/169,868, filed on Jun. 1, 2016, now Pat. No. 9,662,421, which is a continuation of application No. 14/723,727, filed on May 28, 2015, now Pat. No. 9,433,706, which is a continuation of application No. 14/364,756, filed as application No. PCT/IB2013/000873 on Mar. 1, 2013, now Pat. No. 9,090,879.

(60) Provisional application No. 61/611,810, filed on Mar. 16, 2012.

(51) Int. Cl.
| | |
|---|---|
| A61L 27/50 | (2006.01) |
| A61F 2/06 | (2013.01) |
| A61K 35/12 | (2015.01) |
| A61K 35/14 | (2015.01) |
| A61K 35/28 | (2015.01) |
| A61K 35/34 | (2015.01) |
| A61K 35/44 | (2015.01) |
| A61K 35/545 | (2015.01) |
| A61L 27/24 | (2006.01) |
| A61L 27/36 | (2006.01) |
| A61L 27/38 | (2006.01) |
| A61L 27/54 | (2006.01) |
| C12N 5/071 | (2010.01) |
| C12N 5/078 | (2010.01) |

(52) U.S. Cl.
CPC .......... *A61L 27/507* (2013.01); *A61K 35/14* (2013.01); *A61K 35/28* (2013.01); *A61K 35/34* (2013.01); *A61K 35/44* (2013.01); *A61K 35/545* (2013.01); *A61L 27/24* (2013.01); *A61L 27/3616* (2013.01); *A61L 27/3625* (2013.01); *A61L 27/3808* (2013.01); *A61L 27/3826* (2013.01); *A61L 27/3834* (2013.01); *A61L 27/3886* (2013.01); *A61L 27/54* (2013.01); *C12N 5/0641* (2013.01); *C12N 5/0691* (2013.01); *C12N 5/0692* (2013.01); *A61F 2/06* (2013.01); *A61F 2/062* (2013.01); *A61F 2240/001* (2013.01); *A61K 2035/124* (2013.01); *A61L 2300/252* (2013.01); *A61L 2300/64* (2013.01); *A61L 2430/34* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 6,376,244 | B1 | 4/2002 | Atala |
| 6,753,181 | B2 | 6/2004 | Atala |
| 9,090,879 | B2 | 7/2015 | Sumitran-Holgersson et al. |
| 9,433,706 | B2 | 9/2016 | Sumitran-Holgersson et al. |
| 9,662,421 | B2 | 5/2017 | Sumitran-Holgersson et al. |
| 2005/0129681 | A1 | 6/2005 | Varner |
| 2006/0240061 | A1 | 10/2006 | Atala et al. |
| 2007/0208420 | A1 | 9/2007 | Ameer et al. |
| 2007/0260109 | A1* | 11/2007 | Squillace .............. A61L 2/0094 600/36 |
| 2008/0306610 | A1* | 12/2008 | Wang .................. A61L 27/3687 623/23.72 |
| 2013/0028981 | A1* | 1/2013 | Gratzer ............... A61L 27/3641 424/548 |
| 2017/0049935 | A1 | 2/2017 | Sumitran-Holgersson et al. |
| 2017/0071738 | A1 | 3/2017 | Sumitran-Holgersson et al. |

FOREIGN PATENT DOCUMENTS

| | | | | |
|---|---|---|---|---|
| CN | 101474426 A | | 7/2009 | |
| WO | WO-2011132089 A2 | * | 10/2011 | ............ A61L 27/24 |

OTHER PUBLICATIONS

Cartmell et al. "Development of cell-seeded patellar tendon allografts for anterior cruciate ligament reconstruction." Tissue Engineering 10.7-8 (2004): 1065-1075. (Year: 2004).*
Courtman et al. "The role of crosslinking in modification of the immune response elicited against xenogenic vascular acellular matrices." Journal of Biomedical Materials Research 55.4 (2001): 576-586 (Year: 2001).*
Beck et al., Nature Genetics, 2000, 24:23-25.

(Continued)

*Primary Examiner* — Emily A Cordas

(57) ABSTRACT

The present invention relates to methods for recellurization of blood vessels. This method is particularly useful for producing an allogeneic vein, wherein a donor vein is decellularized and then recellularized using whole blood or bone marrow stem cells. The allogeneic veins produced by the methods disclosed herein are particularly advantageous for implantation or transplantation into patients with vascular diseases.

9 Claims, 32 Drawing Sheets

(31 of 32 Drawing Sheet(s) Filed in Color)

(56) References Cited

OTHER PUBLICATIONS

Charles River, Inbred Mice, 2015.
Rohan et al., FASEB J., 2000, 14:872-876.
Zhu et al., Biomater., 2008, 29:2628-2636.
Anonymous, "Perfusion" and "Perfusion Culture," Dictionary of Biochemistry, 3$^{rd}$ Ed., 2000, Imahori Ed., Tokyo Kagaku Dojin Co., Tokyo, JP, p. 340, English translation.
Asahara et al., "Isolation of Putative Progenitor Endothelial Cells for Angiogenesis," Science, Feb. 1997, 275(5302):964-967.
Cho et al., "Small-Diameter Blood Vessels Engineered with Bone Marrow-Derived Cells," Ann. Surg., Mar. 2005, 241(3):506-515.
Dahan et al., "Porcine Small Diameter Arterial Extracellular Matrix Supports Endothelium Formation and Media Remodeling Forming a Promising Vascular Engineered Biograft," Tissue Eng. Part A, Feb. 2012 (Dec. 2, 2011), 18(304):411-422.
Dong et al., "Mesenchymal Stem Cell-Based Tissue Engineering of Small-Diameter Blood Vessels," Vascular, Aug. 2011 (Jul. 22, 2011), 19(4):206-213.
International Search Report and Written Opinion for PCT/EP2015/061736, Jul. 28, 2015, 9 pages.
International Search Report and Written Opinion for PCT/IB2013/000873, Sep. 23, 2013, 12 pages.
Laschke et al., "Endothelial Progenitor Cells Contribute to the Vascularization of Endometriotic Lesions," Am. J. Pathol., Jan. 2011, 178(1):442-450.
Olausson et al., "Transplantation of Allogeneic Vein Bioengineered with Autologous Stem Cells: A Proof-of-Concept Study," Lancet, Jul. 21, 2012 (Jun. 14, 2014) 380(9838):230-237.
Punshon et al., "Assessment of the Potential of Progenitor Stem Cells Extracted from Human Peripheral Blood for Seeding a Novel Vascular Graft Material," Cell. Prolif., Apr. 2008, 41(2):321-335.
Quint et al., "Decellularized Tissue-Engineered Blood Vessel as an Arterial Conduit," PNAS USA, May 31, 2011 (May 12, 2011), 108(22):9214-9219.
Ribatti et al., "Postnatal Vasculogenesis," Mech. Dev., Feb. 2001, 10092):157-163.
Simper et al., Smooth Muscle Progenitor Cells in Human Blood,: Circulation, Sep. 2002, 106(10):1199-1204.
Written Opinion for PCT/IB2013/000873, Sep. 23, 2013, 7 pages.
Zhao et al., "The Development of a Tissue-Engineered Artery Using Decelllularized Scaffold and Autologous Ovine Mesenchymal Stem Cells," Biomaterials, Jan. 2010 (Oct. 12, 2012), 31(2):296-307.
Zhao et al., "Beneficial Effects of Granulocyte-Colony Stimulating Factor on Small-Diameter Heparin Immobilized Decellularized Vascular Graft," J. Biomed. Mater. Res. A, Nov. 2010, 95(2):600-610.
Fitzpatrick et al., "Effect of Decellularization Protocol on the Mechanical Behavior of Porcine Descending Aorta," International Journal of Biomaterials, 2010, Article ID 620503, 11 pages.

\* cited by examiner

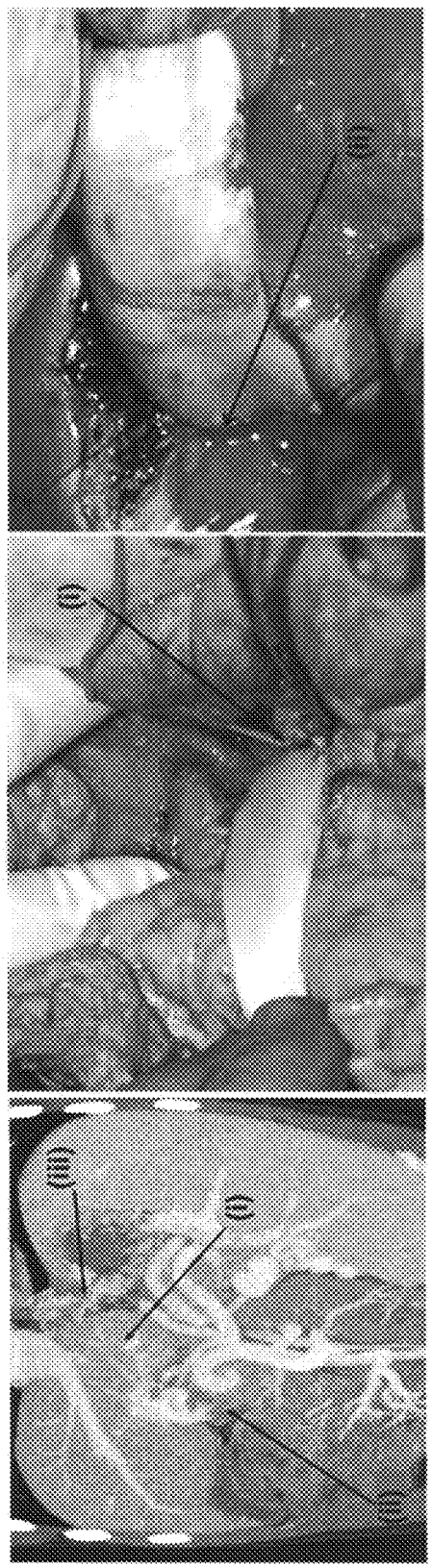

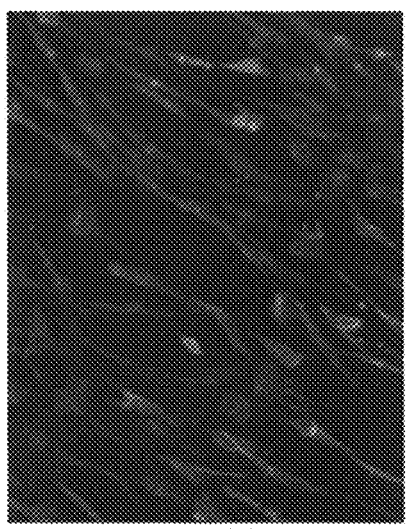
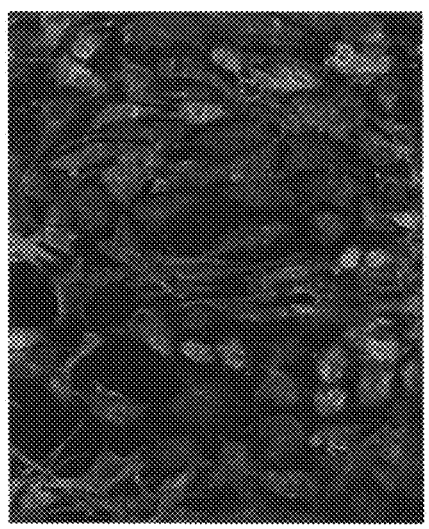
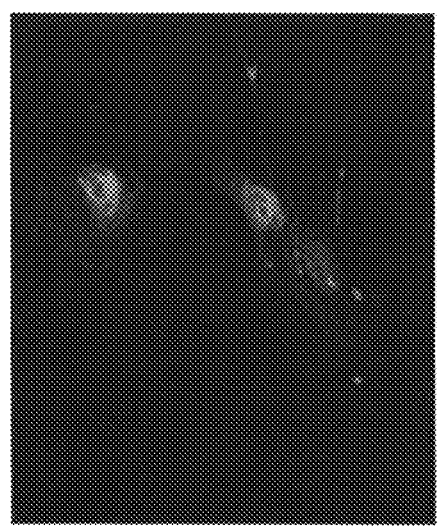
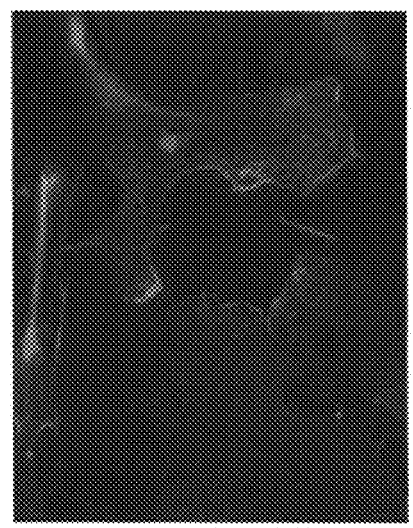
FIG. 3A  FIG. 3B  FIG. 3C  FIG. 3D  FIG. 3E Blue box is the bioreactor.
Red box is the vessel.
The direction of arrows indicate the flow of solutions in the pipes.

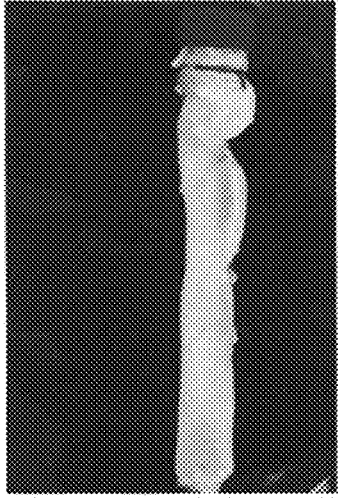
FIG. 7A Normal Veins
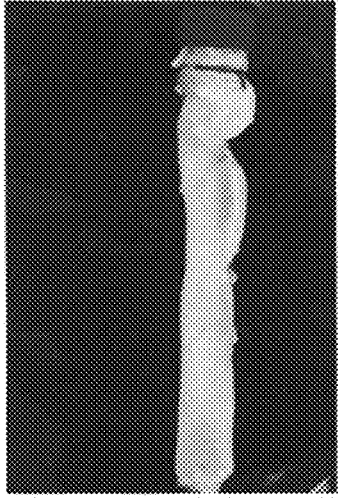
FIG. 7B Decellularized Veins
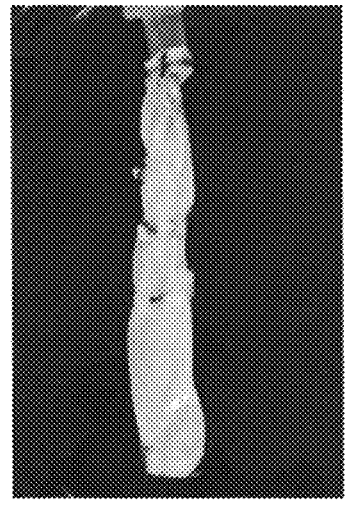
FIG. 7C Normal Veins
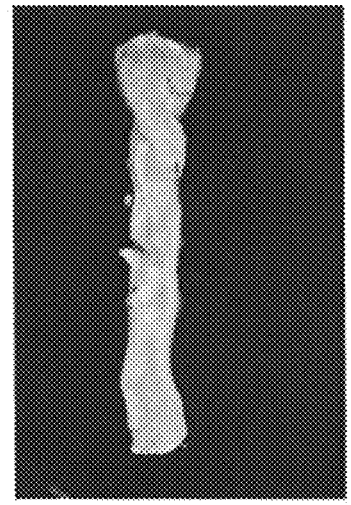
FIG. 7D Decellularized Veins

FIG. 7E Normal Veins
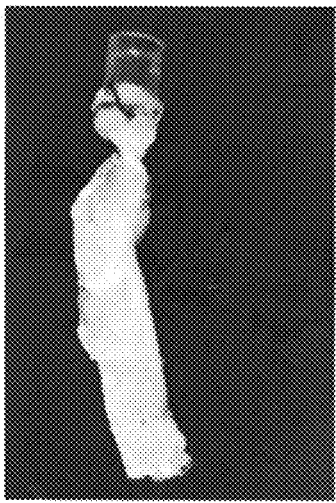
FIG. 7F Decellularized Veins
FIG. 7G Recellularized Veins
Vein 3
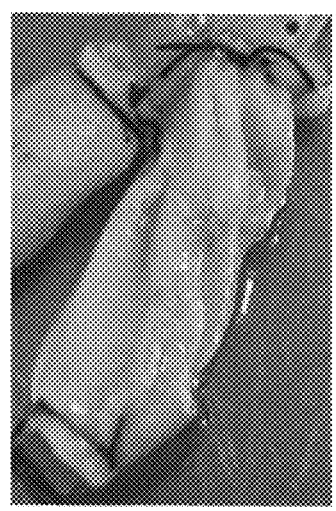
FIG. 7H Normal Veins
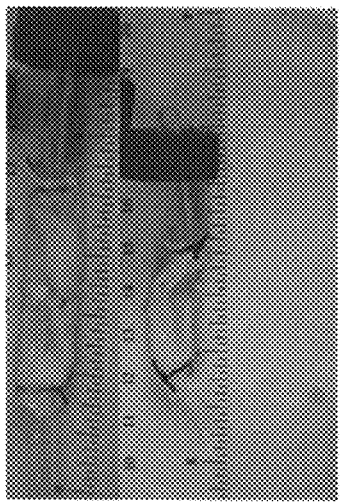
FIG. 7I Decellularized Veins
FIG. 7J Recellularized Veins
Vein 4

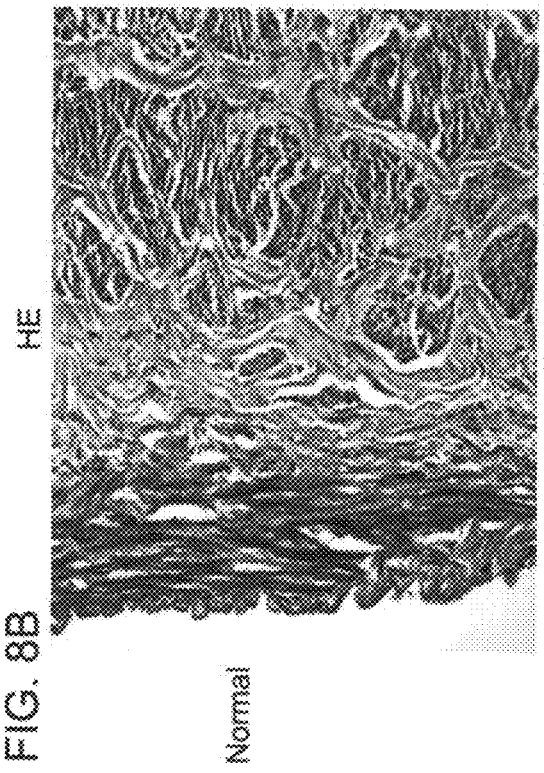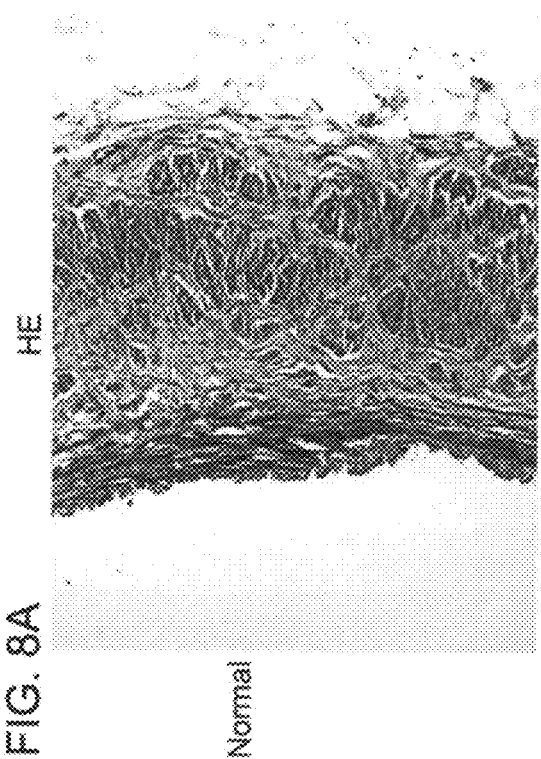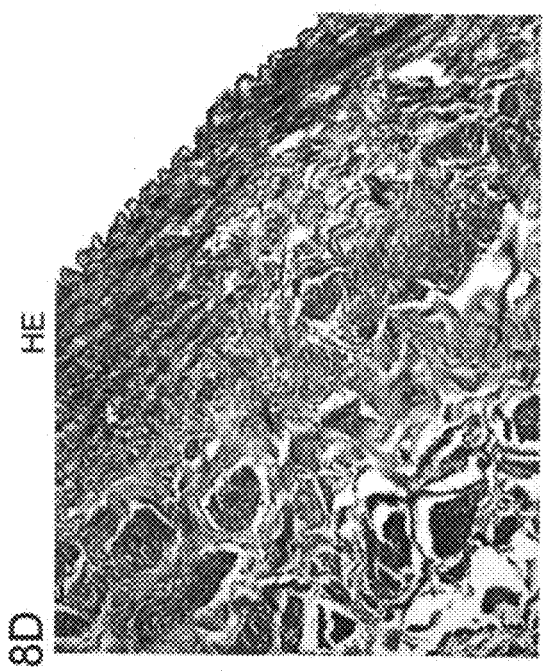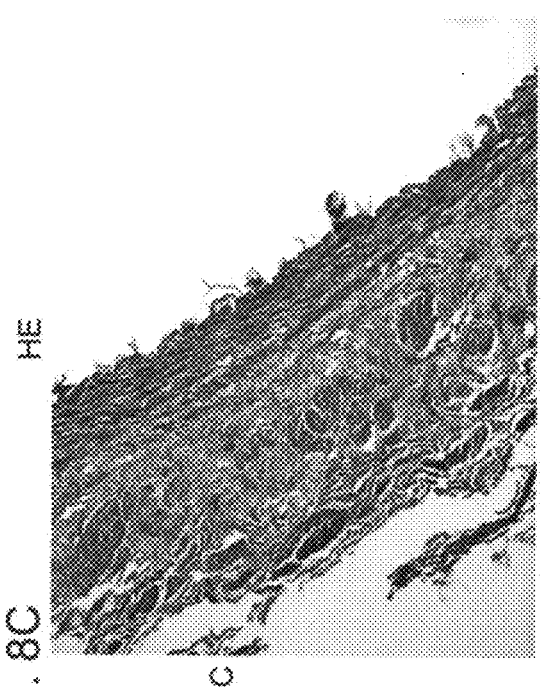

Normal

DC

Normal

DC

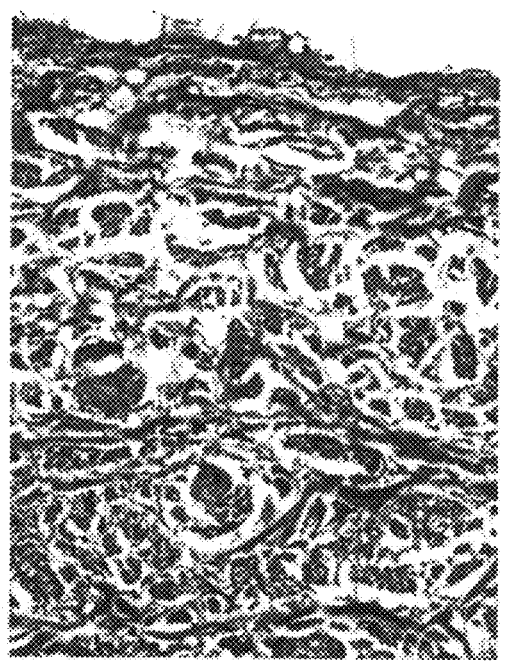
FIG. 10C Normal
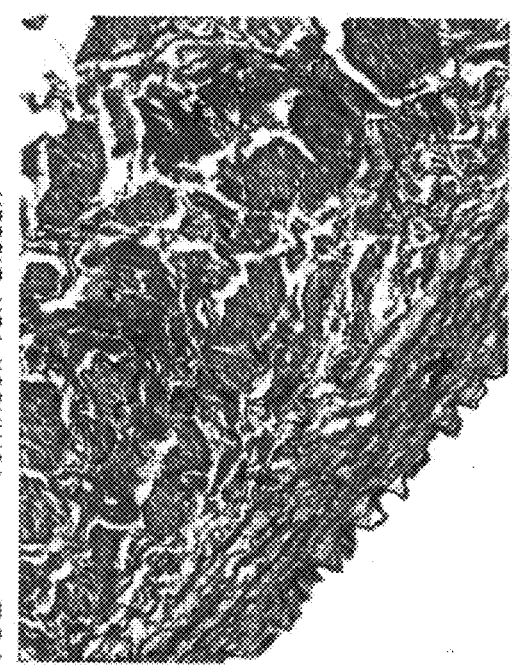
FIG. 10D DC
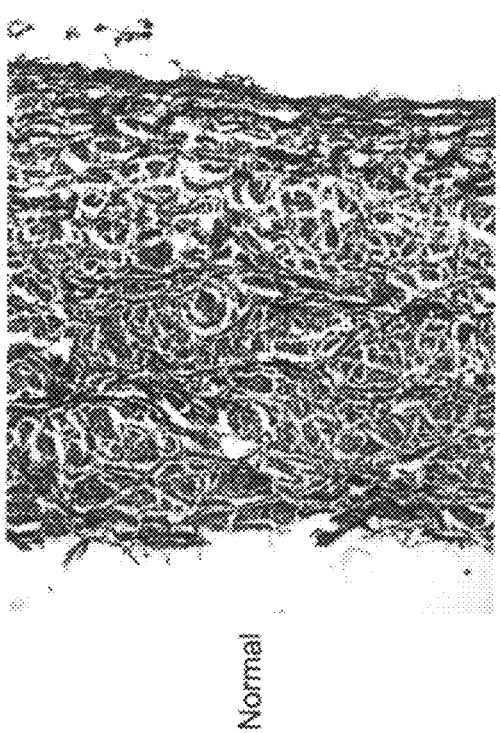
FIG. 10A Normal
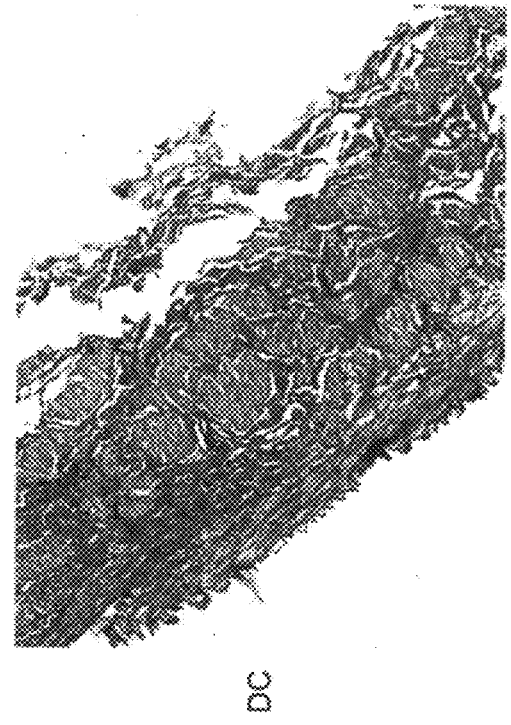
FIG. 10B DC

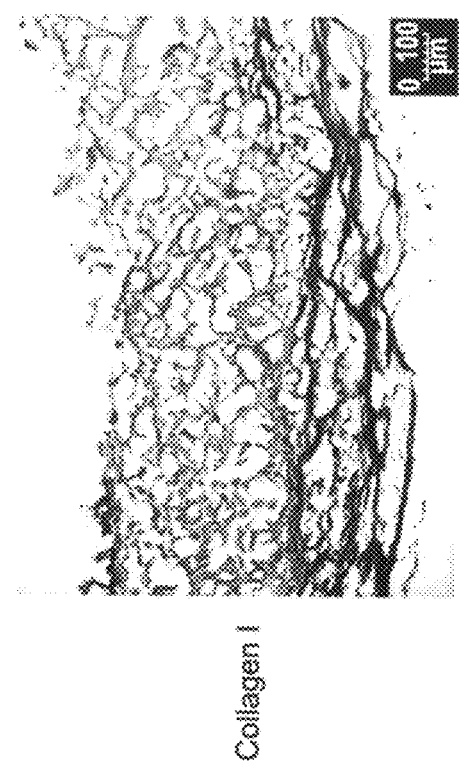
FIG. 11A Collagen I Normal
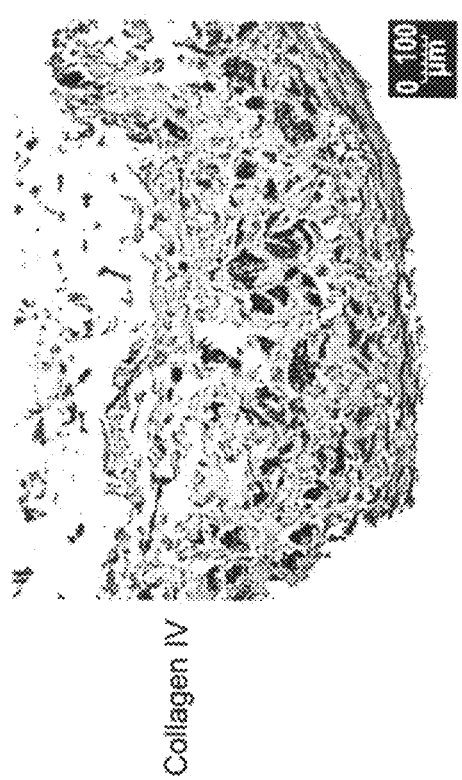
FIG. 11B Collagen IV Normal
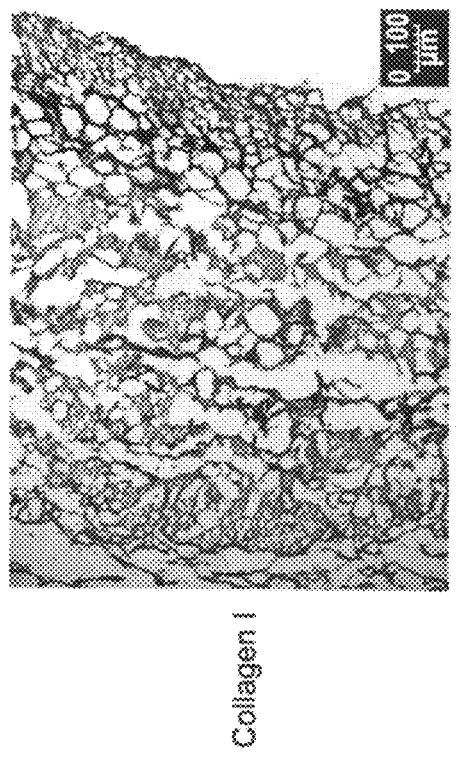
FIG. 11C Collagen I DC
FIG. 11D Collagen IV DC

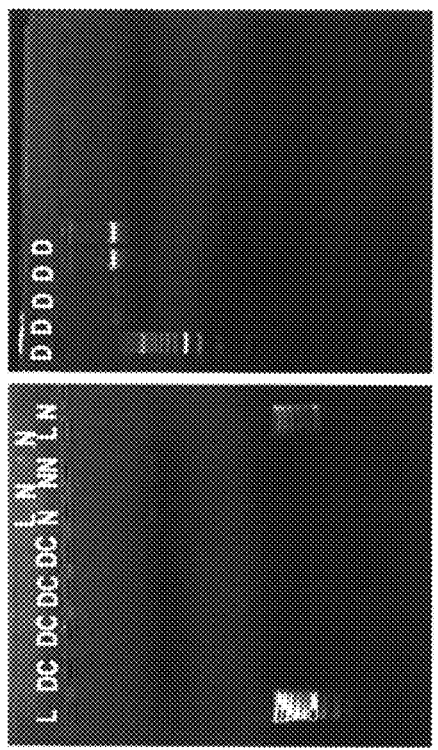

DNA Quantification

| S.No | Sample | DNA ng/mg | Average |
|---|---|---|---|
| 1 | Normal H.Vein (Person 1) | 349.4 | |
| 2 | Normal H.Vein 2 (Person 2) | 161.5 | |
| 3 | Normal H.Vein 3 (Person 2) | 144.06 | 193.85 |
| 4 | Normal H.Vein 4YG | 120.44 | |
| 1 | H.Vein - TNBP - 11 cycles (person 1) | 3.29 | |
| 2 | H.Vein - SDC - 11 cycles (person 1) | -0.49 | |
| 3 | H.Vein 4YG2 DC 9 cycles Thick | 5.98 | 15.506 |
| 4 | H.Vein 4YG2 DC 9 cycles Thin | 29.35 | |
| 5 | H.Vein 1YB DC 9 Cycles | 39.4 | |

FIG. 13B

Collagen Quantification

| S.No | Sample | Conc. ug/mg | Averages | SD | SE |
|---|---|---|---|---|---|
| 1 | Normal Vein 9/812 | 0.542277778 | 0.507721634 | 0.183353685 | 0.107014 |
| 2 | Normal Human Vein 4YG | 0.307521739 | | | |
| 3 | Normal Human Vein 4YG2 | 0.673385385 | | | |
| 1 | Decellularized Human Vein 21 | 0.411638824 | 0.442073536 | 0.03975952 | 0.022955 |
| 2 | Decellularized Human Vein 22 | 0.427533333 | | | |
| 3 | Decellularized Human Vein SDC 12 cycles | 0.487056452 | | | |

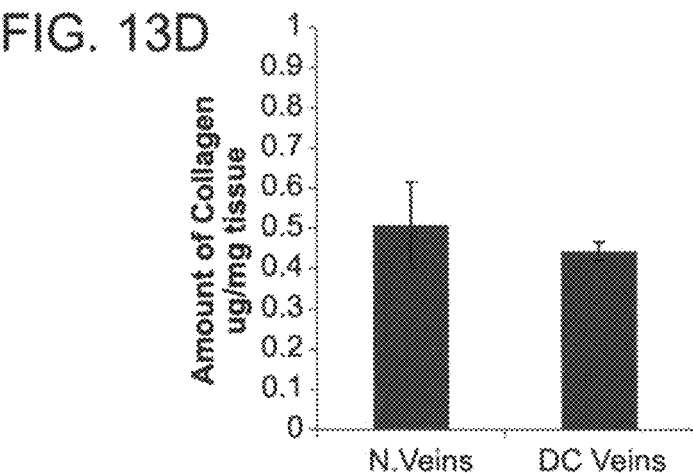
FIG. 13D
FIG. 13E
| GAG's Quantification | | | | | |
|---|---|---|---|---|---|
| S.No | Sample | GAGs (ug/mg) | Average | SD | SE |
| 1 | N.H.Vein with valves | 2.143135593 | | | |
| 2 | N.H.Vein 23 | 2.003486486 | | | |
| 3 | N.H.Vein 4YG | 1.839797688 | | | |
| 4 | N.H.Vein 2 | 2.370978261 | | | |
| 5 | N.H.Vein 4YG2 | 2.243507463 | | | |
| 6 | N.H.Vein oslo | 3.720588235 | 2.386916 | 0.679012 | 0.277206 |
| 7 | DC H.Vein with valves | 1.728933054 | | | |
| 8 | DC H.Vein 21 | 0.596025513 | | | |
| 9 | DC H.Vein 22 | 0.899723 | | | |
| 10 | DC H.Vein TNBP | 2.53835443 | | | |
| 11 | DC H.Vein 4YG2 Thin | 0.442720878 | | | |
| 12 | DC H.Vein 3 Dnase cycles | 0.398645116 | 1.100734 | 0.858188 | 0.350354 |
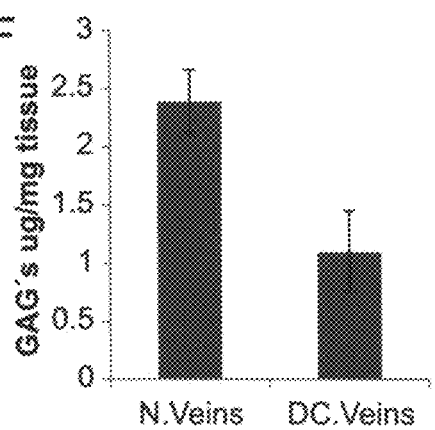
FIG. 13F

| | Luminex | | |
|---|---|---|---|
| S. No | Growth Factor | N. Vein | DC Vein |
| 1 | VEGF-A | 19,9155 | 92,99248 |
| 2 | FGF-2 | 6691,134 | 331,9665 |
| 3 | PLGF | 26,18524 | 6,790597 |
| 4 | G-CSF | 649,2366 | 31,40086 |
| 5 | FGF 1 | 10,0411 | 2,290397 |
| 6 | Follistatin | 142,175 | 80,22624 |
| 7 | IL-8 | 0,462911 | 0,15407 |
| 8 | HGF | 3088,075 | 95,13041 |
| 9 | Angiopoietin-2 | 15,12961 | 0,669507 |
| 10 | Endoglin | 233,4429 | 4,195369 |
| 11 | BMP-9 | 3,73737 | 0,496792 |
| 12 | VEGF-C | 8,62099 | 1,001203 |
| 13 | VEGF-D | 4,028769 | |
| 14 | HB-EGF | 2,084002 | |
| 15 | EGF | 0,628308 | |
| 16 | Endothelin-1 | 73,7502 | |
| 17 | Leptin | 0,40848 | |

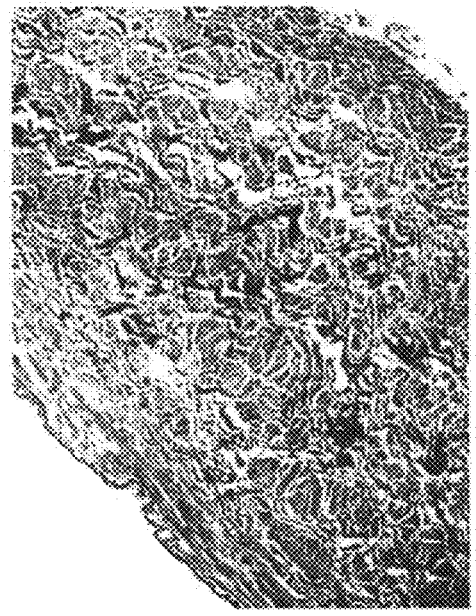
FIG. 16A Massons Trichrome — 4YG2 2 cycles Recellularized
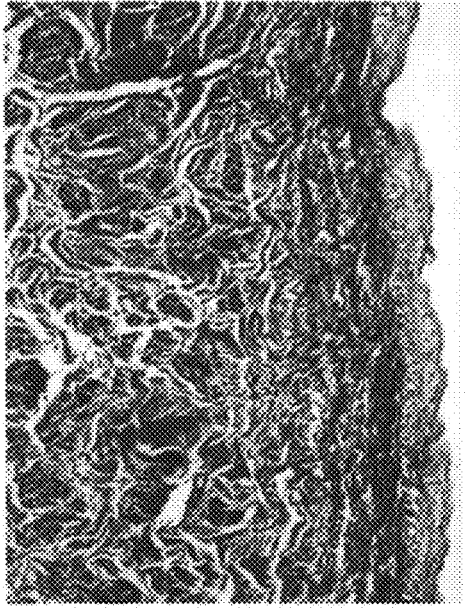
FIG. 16B — 4YG2 2 cycles Recellularized
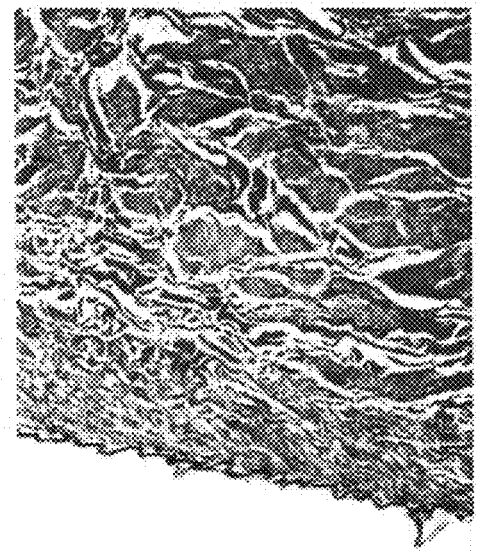
FIG. 16C — 4YG2 4 cycles Recellularized
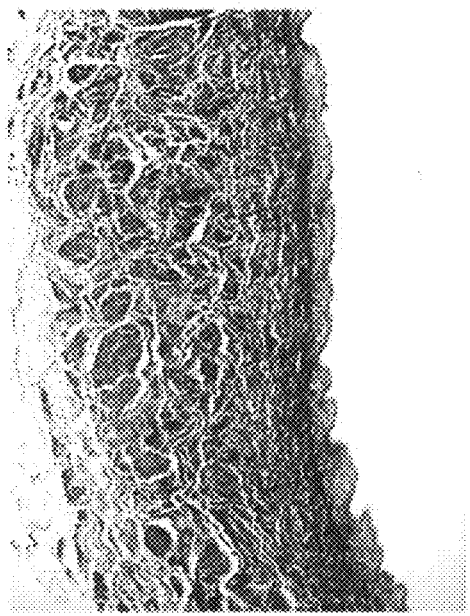
FIG. 16D — 4YG2 4 cycles Recellularized

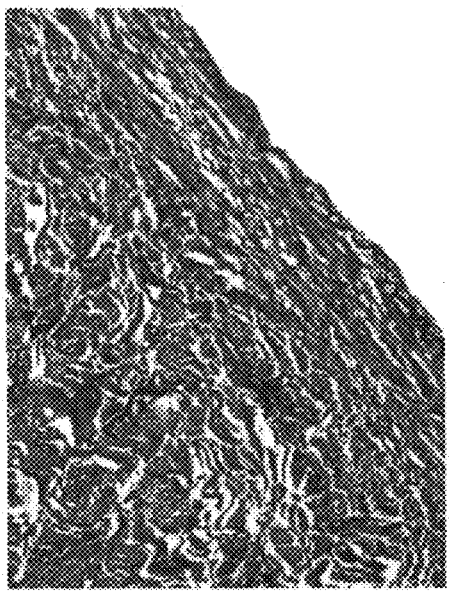
FIG. 17A
FIG. 17B
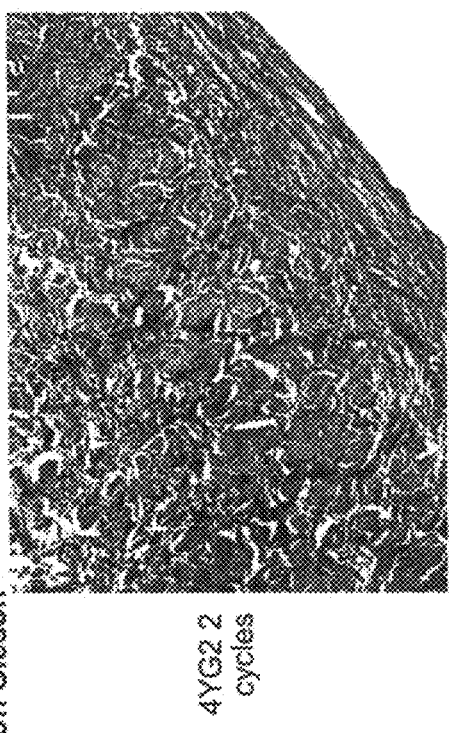
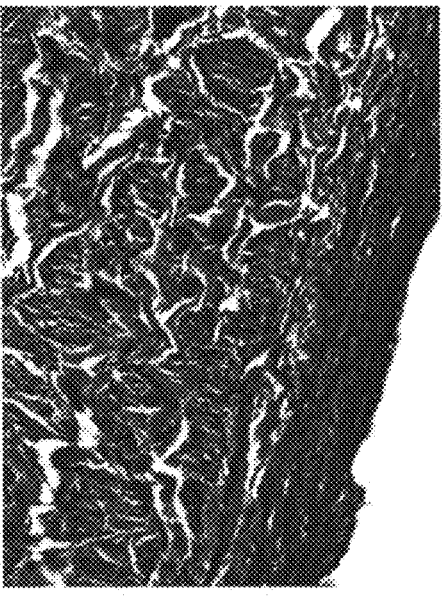
FIG. 17C
FIG. 17D
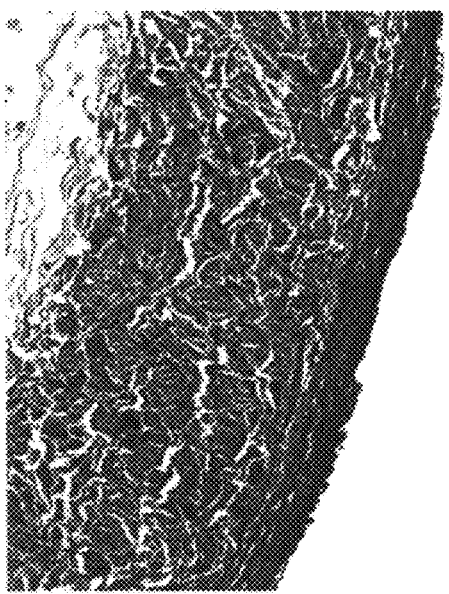

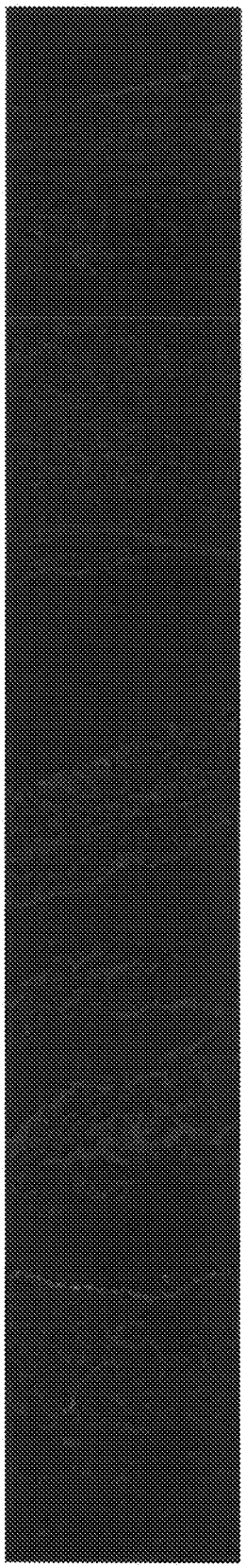
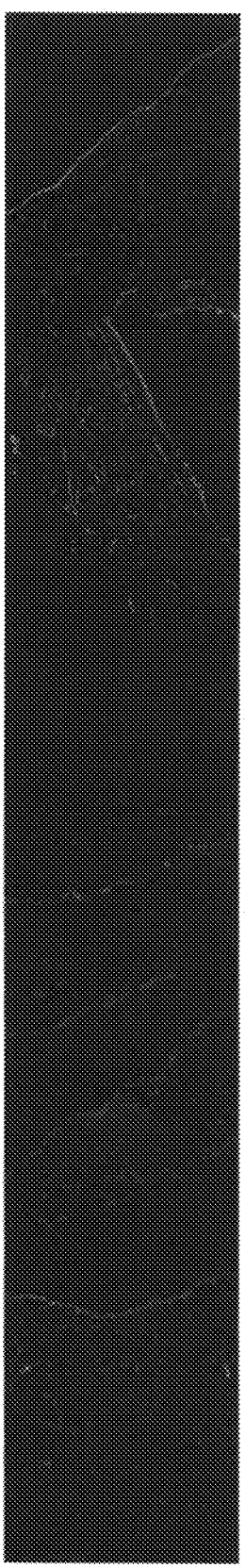
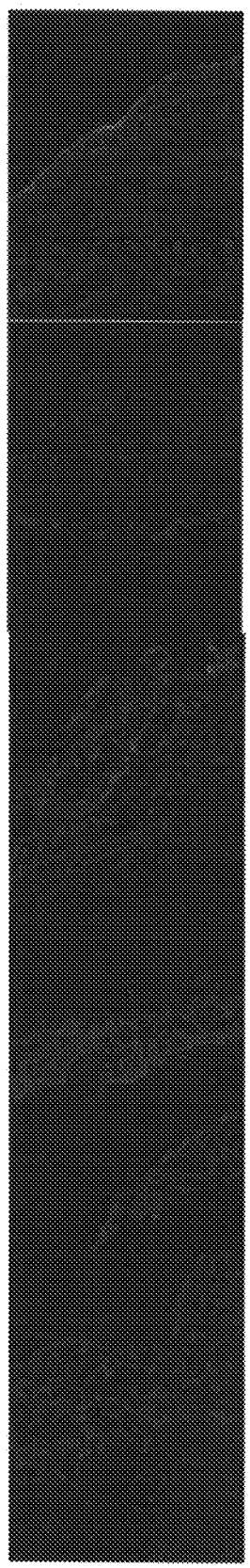
FIG. 18A CD31
FIG. 18B VWF
FIG. 18C SMA

4YG
4 CYCLES

4YG
4 CYCLES

1YG
2 CYCLES

1YG
2 CYCLES

SDC 10 cycles 9.7.12

SDC 10 cycles 9.7.12

SDC 12
27.7
2 cycles

SDC 12
27.7
2 cycles

BIOENGINEERED ALLOGENEIC BLOOD VESSEL

RELATED APPLICATIONS

This application is a Continuation of U.S. application Ser. No. 15/481,862, filed Apr. 7, 2017, (now U.S. Pat. No. 10,517,996) which is a divisional of U.S. application Ser. No. 15/169,868, filed on Jun. 1, 2016, which is a continuation of U.S. application Ser. No. 14/723,727, filed May 28, 2015 (now U.S. Pat. No. 9,433,706), which is a continuation of U.S. application Ser. No. 14/364,756, filed Jun. 12, 2014 (now U.S. Pat. No. 9,090,879), which is a national stage application, filed under 35 U.S.C. § 371, of International Application No. PCT/IB2013/000873, filed Mar. 1, 2013, which claims priority to, and benefit of U.S. Provisional Application No. 61/611,810, filed on Mar. 16, 2012, each of which is herein incorporated by reference it its entirety for all purposes.

BACKGROUND

Vascular diseases are among the increasing health problems experienced by millions of people worldwide. Surgical replacement of blood vessels is often required in common vascular surgical procedures such as coronary bypass heart surgery. Current sources of blood vessels for transplant or implant include the patient's own blood vessels (i.e., from limbs), tissue-matched blood vessels from donors, blood vessels from animals, and artificial blood vessels or synthetic grafts. Unfortunately, these sources of replacement blood vessels have many disadvantages and complications, such as insufficient or lack of usable allogeneic vessels, donor shortage and unavailability, poor patency, transplant rejection, length restrictions, immunosuppression, and thrombotic complications, etc.

Thus, there exists a need for allogeneic blood vessels and methods for their production.

SUMMARY

The present invention features materials and methods for producing an allogeneic blood vessel.

The present invention provides a method of recellularizing a blood vessel comprising introducing a population of cells to a decellularized blood vessel and culturing said population of cells on the decellularized blood vessel, thereby recellularizing the blood vessel.

The present invention features a method for providing a blood vessel graft to a patient comprising delivering a subject-derived population of cells to a decellularized blood vessel; and culturing said population of cells on the decellularized blood vessel. In some aspects, the decellularized blood vessel is from an allogeneic donor.

In one aspect, the population of cells is from whole blood, bone marrow, or a stem cell.

In another aspect, the population of cells comprises endothelial cells and smooth muscle cells. The stem cell is a CD133+ expressing cell.

In another aspect, the population of cells is expanded and differentiated into endothelial cells and smooth muscle cells in vitro prior to introducing the endothelial cells and the smooth muscle cells to the decellularized blood vessel.

In a further aspect, the population of cells is introduced to the decellularized blood vessel by injection or perfusion.

In another aspect, the culturing of the population of cells comprises perfusion of endothelial cell medium and smooth muscle cell medium. The perfusion of the endothelial cell medium and the smooth muscle cell medium is administered in alternation. The administration in alternation is repeated at least twice.

In another aspect, the culturing the population of cells on the decellularized blood vessel results in differentiation of the population of cells to endothelial cells and smooth muscle cells. In some embodiments, the endothelial cells line the exterior of the decellularized blood vessel and said smooth muscle cells line the lumen of the decellularized blood vessel.

In any of the foregoing methods, the endothelial cells express VE-cadherin, AcLDL, vWF or CD31. In any of the foregoing methods, the smooth muscle cells express smooth muscle actin or vimentin.

In one aspect, the culturing of the population of cells is in vitro.

In the blood vessel is a vein or artery.

The present invention features a blood vessel produced by any one of the methods described herein.

The present invention also features the use of a blood vessel produced by any one of the methods described herein for implantation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1E show pictures of the operation area prior to and after the clinical and surgical procedures. (A) Diagnostic CT Angiography before the primary operation. The image shows intra-hepatic portal flow concentrated to the left part of the liver (i). Collaterals feed the portal vein but no external portal vein in continuity can be seen (ii). The spleen is enlarged and collaterals can be found around the esophagus and in the liver hilum. (B-C) Successful surgical correction using a graft between the SMV and the left portal vein (meso-Rex). The stem-cell derived vein is anastomosed to the SMV (i) The vein graft is anastomosed to the left portal vein (ii) Peroperative ultrasound showing blood flows of 25-40 cm/s in the graft and in the intra-hepatic portal vein. (E) CT Angiography showing a patent graft (i), 1 week after surgery. The image has been reconstructed using 3-4 images to better visualize the orientation of the graft.

FIGS. 3A-3E show immunofluorescence staining of recipient's endothelial and smooth muscle cells grown on chamber slides. Cells stained positive for the antibodies are green, nuclei are blue. Endothelial cells are positive for VE-Cadherin (A), AcLDL (C) and vWF (D). Smooth muscle cells stained positive for their specific markers alpha-actin (B) and vimentin (E). FIGS. 3A, 3C, and 3D magnification 40× and FIGS. 3B and 3E are magnification 20×.

FIGS. 7A-7J show a series of photographs of four donor veins (left photographs), after decellularization (middle photographs), and after recellularization (right photographs).

FIGS. 8A-8D show histological analysis by HE staining of nuclei in normal veins (top panels, A-B) and decellularized veins (DC, bottom panels, C-D). No staining for nuclei was observed after 9 cycles of decellularization.

FIGS. 10A-10D show histological analysis by Vernhoeff Von Gieson (VVG) staining of normal veins (top panels, A-B) and decellularized veins (DC, bottom panels, C-D). No staining for nucleic was observed after 9 cycles of decellularization. VVG staining also showed the preservation of elastin (and elastin ring) and collagen in decellularized veins.

FIGS. 11A-11D show histological analysis by staining of normal veins (left panels, A-B) and decellularized veins (DC, right panels, C-D). Staining showed the preservation of Collagen I (top panels, A, C) and Collagen IV (bottom panels, B, D) in decellularized veins.

FIGS. 13A-13F show the quantification of DNA (A), collagen, and glycosaminoglycans (GAGs) levels after decellularization, as determined by gel electrophoresis, sircol, and bislycan assays, respectively. DNA gel (top right panel, C) shows ladder control (L), decellularized veins (DC) and normal veins (N). Collagen levels were measured by sircol assay: raw data is presented in the table (middle left, B) and quantification is represented in the graph (middle right, D). Glycosaminoglycan (GAG) levels were measured by bislycan assay: raw data is presented in the table (bottom left, E) and quantification is represented in the graph (bottom right, F).

FIGS. 16A-16D show histology staining with Massons Trichrome (MT) and confirms presence of nuclei, cytoplasm, and attachment of cells to collagen.

FIGS. 17A-17D show histology staining with Vernhoeff Von Giesen (VVG) and confirms the presence of nucleic, cytoplasm, and attachment of cells to collagen.

FIGS. 18A-18C show immunofluorescence staining for endothetlial and smooth muscle cell markers. CD31 (top panels, A) and VWF (middle panels, B) staining confirmed the presence of endothelial cells towards the inner lining of the vein. SMA (bottom panels, C) staining confirmed the presence of smooth muscle cells.

DETAILED DESCRIPTION

Figure 1D:
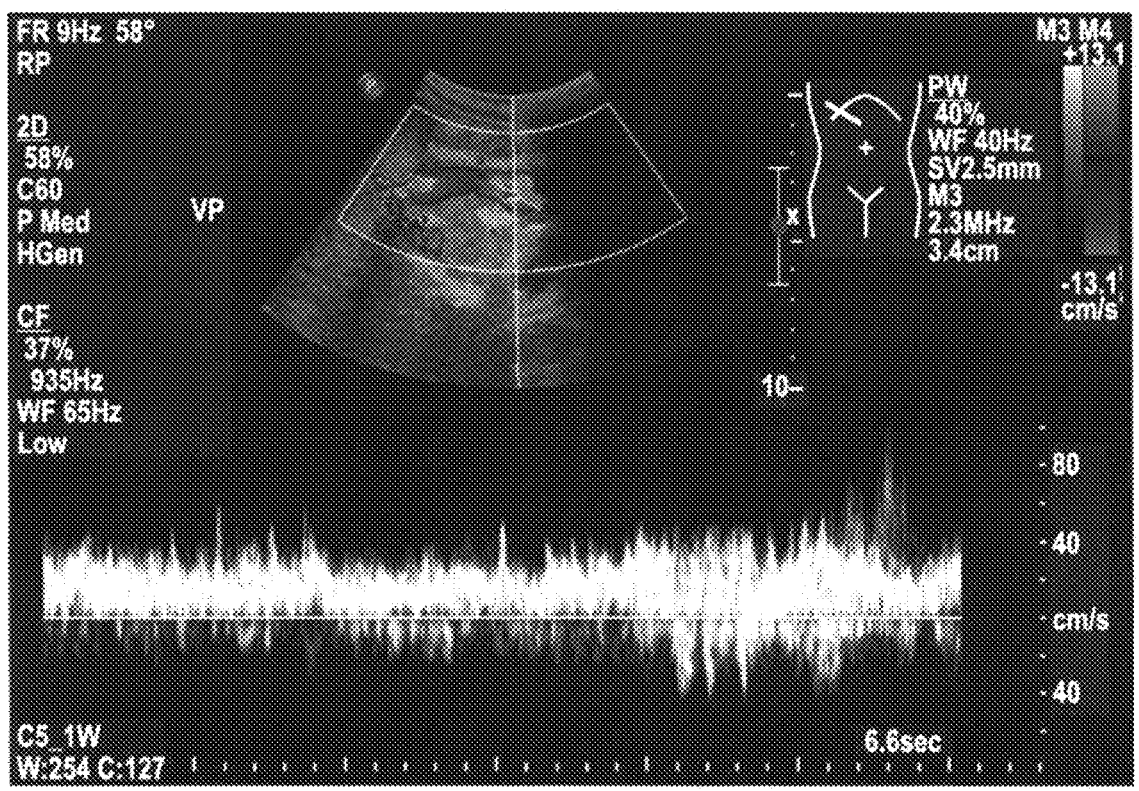

The present invention is based on the surprising discovery that blood vessels suitable for surgical implantation can be successfully bioengineered from a deceased donor vein that was decellularized and later recellularized by autologous cells from the recipient of the graft. This approach can be considered for patients in need of bypass surgery or vascular vein shunts due to thrombosis, chronic deep vein incompetence, vein obstruction or venous reflux. Further, this technique obviates the need for life-long immunosuppression, and is a promising and safe clinical approach with great benefits and lower risks than previous vascular transplant solutions.

The present invention provides methods for decellularizing a blood vessel. Methods for decellularization of blood vessels encompass the removal of endogenous cells while preserving integrity of the extracellular matrix (ECM) are described herein. The process of decellularization as described herein utilizes sequential treatment of two or more different cellular disruption solutions, in several cycles. In a preferred embodiment, decellularization may be achieved when no nuclei remains, as detected by various methods known in the art. The blood vessel may be a vein or an artery. The blood vessel may be from a donor. In some embodiments, the donor is deceased. In other embodiments, the donor may be from a HLA or tissue-matched donor.

The present invention also provides methods for recellularization of the decellularized blood vessel, comprising introducing a population of cells to the decellularized blood vessel and culturing said population of cells on and in the decellularized blood vessel. Methods described herein are useful for the expansion of the population of cells and differentiation of the population of cells to functional endothelial cells and smooth muscle cells to produce a functional blood vessel.

In one embodiment, the population of cells utilized for recellularization are derived from stem or progenitor cells, for example, bone-marrow-derived stem or progenitor cells, or cells expressing CD133 (CD133+ cells). Stem or progenitor cells can be expanded and differentiated in vitro into endothelial cells and/or smooth muscle cells by methods known in the art. For example, stem or progenitor cells can be cultured in the presence of certain growth factors and supplements that initiate differentiation into endothelial cells and/or smooth muscle cells. In some aspects, the differentiated cells may not be terminally differentiated, but express at least one endothelial cell marker (i.e., CD31 or vWF) or at least one smooth muscle cell marker (i.e., smooth muscle actin) prior to introduction to the decellularized blood vessel. The endothelial cells and smooth muscle cells derived from the stem cell as described herein are introduced to the decellularized blood vessel, for example, by perfusion. Culturing of the endothelial cells and smooth muscle cells comprise incubating the cells and blood vessel with endothelial cell medium or smooth muscle cell medium in alternating cycles until the desired recellularization is achieved.

Post natal vasculogenesis is the formation of new blood vessels in adults by circulating endothelial progenitor cells (EPCs); and angiogenesis is formation of new blood vessels from pre-existing endothelial cells (Ribatti D et al., 2001). These two processes contribute in formation of vessel branches and in pathogenic states like wound healing, ischaemia, fracture healing, tumor growth etc., (Laschke etal, 2011). There are endothelial cells and endothelial progenitor cells co-existing in circulation in whole blood, and the endothelial progenitor cells contribute to vascularization (Asahara T etal., 1997). Furthermore, progenitor cells for smooth muscle cells are also present in circulating whole blood (Simper D et al., 2002).

In another embodiment, the population of cells utilized for recellularization is from whole blood. Use of whole blood for regeneration of a decellularized blood vessel, would result in efficient recellularization of blood vessels without the need to isolate and expand subpopulations of angiogenic progenitor cells from bone-marrow or whole blood. Whole blood is introduced to the decellularized blood vessel, for example, by perfusion.

There are many advantages of the present invention over the options for vascular grafts currently available. The present invention provides an autologous engineered blood vessel with the following advantages: 1) is non-immunogenic and therefore having minimal risk of graft rejection or adverse immune response; 2) obviates the need for immunosuppression, and therefore less risk to the patient after surgery and for their lifetime; 3) has no length restriction; 4) is more readily available, as compared to matched donor blood vessels or autologous blood vessels; 5) is composed of natural components (i.e., ECM, endothelial cells and smooth muscle cells), and therefore has superior qualities to mostly synthetic and artificial blood vessels, including preserving residual angiogenic growth factors and biomechanical integrity; 6) production of blood vessel is minorly invasive in comparison to harvesting autologous blood vessel for transplant; 7) use of whole blood cells allows rapid and minimally invasive procedure to subject.

As used herein, a "subject" includes a mammal. The mammal can be e.g., any mammal, e.g., a human, primate, bird, mouse, rat, fowl, dog, cat, cow, horse, goat, camel, sheep or a pig. Preferably, the mammal is a human. As used herein, a "subject in need thereof" is a subject having a vascular disease or disorder that requires a vascular graft or transplant, or a subject having an increased risk of developing a vascular disease or disorder that requires a vascular graft or transplant relative to the population at large.

Decellularization of Blood Vessels

The invention provides for methods and materials to decellularize a blood vessel. As used herein, "decellularization" refers to the process of removing cells from a blood vessel, such that the three-dimensional structure of the extracellular matrix (ECM) scaffold remains. Physical methods and chemical and biologic agents are used in combination to lyse cells, often followed by a rinsing step to remove cell remnants and debris. Effective decellularization is dictated by factors such as tissue density and organization, geometric and biologic properties desired for the end product, and the targeted clinical application. Decellularization of blood vessels with preservation of the ECM integrity and bioactivity can be optimized by those skilled in the art, for example, by choosing specific agents and techniques during processing.

The most effective agents for decellularization will depend on many factors including cellularity, density, lipid content, and thickness of the vessel. It should be understood that while most cell removal agents and methods may alter ECM composition and cause some degree of ultrastructure disruption, minimization of these undesirable effects is preferred. One skilled in the art could readily optimize the decellularization process, as described herein, to minimize the disruption of the ECM scaffold.

One or more cellular disruption solutions can be used to decellularize blood vessel. A cellular disruption solution generally includes at least one detergent, such as SDS, PEG, or Triton™ X (a non-ionic octylphenol ethoxylate detergent). A particularly preferred detergent is Triton™ X (a non-ionic octylphenol ethoxylate detergent). A cellular disruption solution can include water such that the solution is osmotically incompatible with the cells. Alternatively, a cellular disruption solution can include a buffer (e.g., PBS) for osmotic compatibility with the cells. Cellular disruption solution also can include enzymes such as, without limitation, one or more collagenases, one or more dispases, one or more DNases, or a protease such as trypsin. In some instances, cellular disruption solution also or alternatively can include inhibitors of one or more enzymes (e.g., protease inhibitors, nuclease inhibitors, and/or collagenase inhibitors).

In certain embodiments, the vessel may be treated sequentially with two or more different cellular disruption solutions. For example, a first cellular disruption solution contains 1% Triton™ X-100 (2-[4-(2,4,4-trimethylpentan-2-yl) phenoxy]ethanol) (×100, Sigma, Sweden), a second cellular disruption solution contains 1% tri-n-butyl phosphate (TNBP) 28726.1, VWR, Sweden), and a third cellular disruption solution contains 0.004 mg/ml deoxyribonuclease I (DNase I) (D7291, Sigma, Sweden). Sequential treatment may include repeating treatment with at least one of the cellular disruption solutions in the treatment sequence. In some aspects, the vessel may be treated by decellularization cycles comprising the sequential treatment of one or more cellular disruption solutions in the same order until the desired level of decellularization is achieved. In some embodiments, the preferred number of decellularization cycles is at least 2, at least 3, at least 4, at least 5, at least 6, at least 7, at least 8, at least 9, at least 10, at least 11, at least 12, at least 13, at least 14, at least 15, at least 16, at least 17, at least 19, or at least 20 cycles. The number of cycles needed for desired decellularization is determined through monitoring for presence of nuclei, HLA class I or II antigens, and other indications of presence of cells in the vessels. The preferred level of decellularization is indicated by the lack of nuclei present on the decellularized blood vessel.

In some embodiments, each cellular disruption solution may further comprise additional components, such as antibiotics (i.e., penicillin, streptomycin, and amphotericin), ethylenediaminetetraaceticacid (EDTA) disodium salt dehydrate (EDTA), and/or phenyl methyl sulfonyl fluoride (PMSF). For example, a cellular disruption solution that comprises DNase I may also include calcium chloride and magnesium chloride (A12858, Life Technologies) to activate the enzyme.

Perfusion methods may be used to treat the vessel with cellular disruption solutions for decellularization of the blood vessel. Alternating the direction of perfusion (e.g., antegrade and retrograde) can help to effectively decellularize the blood vessel. Decellularization as described herein essentially decellularizes the vessel from the inside out, resulting in very little damage to the ECM. Depending upon the size and weight of the tissue and the particular detergent(s) and concentration of detergent(s) in the cellular disruption solution, a vessel generally is perfused from about 2 to about 12 hours per gram of tissue with cellular disruption medium. Including washes, an organ may be perfused for up to about 12 to about 72 hours per gram of tissue. Perfusion generally is adjusted to physiologic conditions including pulsatile flow, rate and pressure. Perfusion decellularization as described herein can be compared to immersion decellularization as described, for example, in U.S. Pat. Nos. 6,753,181 and 6,376,244.

In a preferred embodiment, the vessel may be filled with cellular disruption solutions and simultaneously agitated for decellularization of the blood vessel. Different cellular disruptions solutions may be added in a sequential order, and the order repeated multiple times until the desired level of decellularization is achieved. For example, one end of the vein may be kept open while the rest of the openings (i.e., abrasions and branches) were sutured to prevent leakage. The vein may be first rinsed in PBS containing antibiotics (0.5% penicillin, 0.5% streptomycin and 0.5% amphotericin B). Then the vein may be rinsed in distilled water for 72 hours. Each decellularization cycle preferably consists of incubation with 1% Triton™ X (a non-ionic octylphenol ethoxylate detergent) for 3 hours, followed by 1% TnBP for 3 hours, and 0.004 mg/ml DNase I for three hours. Lastly, the vessel may be washed with distilled water overnight to remove cell debris. In each incubation, the vein may be filled with the cellular disruption solution and may be clamped closed. Then the vein may be placed on an agitator at 37. degree. C. for the incubation time (3 hours or overnight) with gentle shaking. At the end of each incubation, the contents of the vessel may be removed and the vessel was rinsed with PBS. After 7-9 cycles (of Triton™ X (a non-ionic octylphenol ethoxylate detergent), TnBP, DNaseI and water wash) plus agitation, the vein may be washed continuously for 48 hours with PBS, where the PBS was replaced every 6 hours. Varying concentrations of detergent (Triton™ X (a non-ionic octylphenol ethoxylate detergent) or TnBP) can be utilized, as needed or to the discretion of one ordinarily skilled in the art. Varying concentrations of enzymes, such as DNase, can be utilized, as needed or to the discretion of one ordinarily skilled in the art.

Optionally, the decellularized vessel can be sterilized prior to recellularization steps. For example, the decellularized vessel is incubated in 0.1% peracetic acid in sterile PBS for 1 hour, followed by washing with sterile water and PBS for 4 hours with each solution.

As indicated herein, a decellularized vessel consists essentially of the extracellular matrix (ECM) components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. Successful decellularization is defined as the absence of detectable myofilaments, endothelial cells, smooth muscle cells, and nuclei in histologic sections using standard histological staining procedures. Preferably, but not necessarily, residual cell debris also has been removed from the decellularized organ or tissue.

To effectively recellularize and generate an allogeneic blood vessel, it is important that the morphology and the architecture of the ECM be maintained (i.e., remain substantially intact) during and following the process of decellularization. "Morphology" as used herein refers to the overall shape of the organ or tissue or of the ECM, while "architecture" as used herein refers to the exterior surface, the interior surface, and the ECM therebetween. The morphology and architecture of the ECM can be examined visually and/or histologically to verify that the decellularization process has not compromised the three-dimentional structure and bioactivity of the ECM scaffold. Histological analysis by staining (i.e., H&E, MT or VVG) may be useful to visualize decellularized blood vessel architecture and preservation of ECM components, such as collagen I, collagen IV, laminin and fibronectin. Other methods and assays known in the art may be useful for determining the preservation of ECM components, such as glycosaminoglycans and collagen. Importantly, residual angiogenic or growth factors remain associated with the ECM scaffold after decellularization. Examples of such angiogenic or growth factors include, but are not limited toVEGF-A, FRF-2, PLGF, G-CSF, FGF-1, Follistatin, HGF, Angiopoietin-2, Endoglin, BMP-9, HB-EGF, EGF, VEGF-C, VEGF-D, Endothelin-1, Leptin, and other angiogenic or growth factors known in the art.

Recellularization of Blood Vessels

The invention provides for materials and methods for generating a regenerated blood vessel. A regenerated blood vessel can be produced by contacting a decellularized blood vessel from a donor as described herein with a population of cells and culturing said population of cells on and in the decellularized blood vessel. As used herein, "recellularization" refers to the process of introducing or delivering cells to a decellularized blood vessel or ECM scaffold, and culturing the cells such that the cells proliferate and/or differentiate to eventually regenerate a blood vessel with architecture, cell organization, and bioactivity similar to that of normal blood vessels.

The population of cells as used herein may be any cells used to recellularize a decellularized blood vessel. These cells can be totipotent cells, pluripotent cells, or multipotent cells, and can be uncommitted or committed. In addition, cells useful in the present invention can be undifferentiated cells, partially differentiated cells, or fully differentiated cells. Cells useful in the present invention also include progenitor cells, precursor cells, and "adult"-derived stem cells. Examples of cells that can be used to recellularize a blood vessel include, but are not limited to, bone marrow-derived stem or progenitor cells, bone marrow mononuclear cells, mesenchymal stem cells (MSC), mutltipotent adult progenitor cells, whole-blood derived stem or progenitor cells such as endothelial stem cells, endothelial progenitor cells, smooth muscle progenitor cells, whole blood, peripheral blood, and any cell populations that can be isolated from whole blood. In some embodiments, the population of cells used to recellularize the blood vessel is allogeneic. "Allogeneic" as used herein refers to cells obtained from the same species as that from which the organ or tissue originated (i.e., self or related or unrelated individuals.). In a particularly preferred embodiment, the cells are from the recipient (i.e., "autologous").

The population of cells may be a heterogeneous population of cells. For example, the cells may be whole blood cells, or from whole blood. These cells include red blood cells, white blood cells, thrombocytes, endothelial cells, endothelial progenitor cells, and smooth muscle progenitor cells. It is known in the art that circulating endothelial cells, endothelial progenitor cells, and progenitor cells for smooth muscle cells can contribute to vasculogenesis and angiogenesis. Thus, application of whole blood cells can readily supply a decellularized blood vessel with cells capable of expanding and differentiating into endothelial and smooth muscle cells for the regeneration of the blood vessel.

The population of cells utilized for recellularization may be isolated from a heterogeneous population of cells. In one embodiment, the population of cells may be stem or progenitor cells isolated from bone marrow. In another embodiment, the population of cells may be endothelial cells or endothelial progenitor cells isolated from whole blood. Methods for isolating particular populations of cells from a heterogeneous population are known in the art. Such methods include lymphotrap, density gradients, differential centrifugation, affinity chromatography, and FACS flow cytometry. Markers known in the art that identify particular populations of cells of interest may be used to isolate the cells from the heterogeneous population. For example, CD133 is known to be expressed on the surface of stem cells or stem-like cells derived from the bone marrow. Selection for CD133+ cells can be achieved by utilization of MACs beads and specific antidbodies that recognize CD133. Markers specific for endothelial progenitor or smooth muscle cell progenitor cells can also be utilized to purify the population of cells of interest.

In some aspects, the population of cells may be cultured in vitro prior to introduction to the decellularized blood vessel. The purpose of culturing in vitro include expanding cell numbers and differentiating cells to specific cell lineages of interest. In some embodiments, the population of cells may be first isolated from a heterogeneous population prior to culturing in vitro. In some embodiments, the population of cells may be bone marrow-derived stem or progenitor cells (i.e CD133+ cells) and may be differentiated in vitro prior to introduction to the decellularized blood vessel. Various differentiation protocols are known in the art and include, for example, growing cells in growth media supplemented with factors, agent, molecules or compounds that induce differentiation into endothelial cells or smooth muscle cells.

The number of cells that is introduced to a decellularized blood vessel in order to generate a blood vessel may be dependent on the size (i.e., length, diameter, or thickness) of the vessel and the types of cells used for recellularization (i.e., stem cells vs. more differentiated cells, such as whole blood). Different types of cells may have different tendencies as to the population density those cells will reach. By way of example, a decellularized organ or tissue can be "seeded" with at least about 1,000 (e.g., at least 10,000, 100,000, 1,000,000, 10,000,000, or 100,000,000) cells; or can have from about 1,000 cells/mg tissue (wet weight, i.e., prior to decellularization) to about 10,000,000 cells/mg tissue (wet weight) attached thereto.

The population of cells can be introduced ("seeded") into a decellularized blood vessel by injection into one or more locations. In addition, more than one type of cell (i.e., endothelial cells or smooth muscle cells) can be introduced into a decellularized blood vessel. For example, endothelial cells can be introduced to the exterior of the decellularized blood vessel, while smooth-muscle cells can be introduced to the lumen of the blood vessel. Alternatively, or in addition to injection, the population of cells can be introduced by perfusion into a cannulated decellularized blood vessel. For example, the population of cells can be introduced to a decellularized blood vessel by perfusion. After perfusion of the cells, expansion and/or differentiation media may be perfused through the blood vessel to induce growth and/or differentiation of the seeded cells. In some embodiments, anti-coagulant agents, such as heparin, may be administered prior to and/or simultaneously to the introduction the population of cells.

Expansion and differentiation media, as used in the present invention, includes cell growth medium containing supplements and factors required for proliferation of endothelial cell or smooth muscle cell, and differentiation to endothelial cell or smooth muscle cell. In some embodiments, the differentiation medium for endothelial cells may be the same as the growth/proliferation medium for endothelial cells. For example, additional factors or supplements present in endothelial growth or differentiation media may include, but are not limited to: ascorbic acid, hydrocortisone, transferrin, insulin, recombinant human VEGF, human fibroblast growth factor, human epithelial growth factor, heparin and gentamycin sulfate. In some embodiments, the differentiation medium for smooth muscle cells may be the same as the growth/proliferation medium for smooth muscle cells. For example, additional factors or supplements present in endothelial growth or differentiation media may include, but are not limited to: smooth muscle growth supplement, smooth muscle differentiation supplement, MesenPro RS™ medium, and transforming growth factor 1. At minimum, growth and differentiation media comprise a base media (i.e., MCDB131, M231, or DMEM) heat inactivated serum (for example, at 10%), glutamine and antibiotics (i.e., penicillin, streptomycin, amphotericin).

In some embodiments, the seeded blood vessel may be incubated or perfused with endothelial cell media and smooth muscle cell media in alternation until the desired recellularization is achieved. In some embodiments, the perfusion of endothelial cell media and smooth muscle cell media in alternation can also be repeated multiple times, for example, at least once, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times or at least 15 times. In some embodiments, the duration of perfusion of endothelial cell media may be the same as the duration of perfusion of smooth muscle cell media. Alternatively, the duration of perfusion of endothelial cell media may be different from the duration of perfusion of smooth muscle cell media. Duration of perfusion of either differentiation or growth media may be dependent on the characteristics of the population of cells seeded on the decellularized blood vessel. Duration of perfusion of the differentiation and growth media may be determined by one skilled in the art.

During recellularization, the decellularized blood vessel may be maintained under conditions in which at least some of the seeded cells can multiply and/or differentiate within and on the decellularized blood vessel. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized blood vessel and the cells attached thereto are maintained in a suitable environment. For example, the cells may require a nutritional supplement (e.g., nutrients and/or a carbon source such as glucose), exogenous hormones or growth factors, and/or a particular pH.

Figure 6:
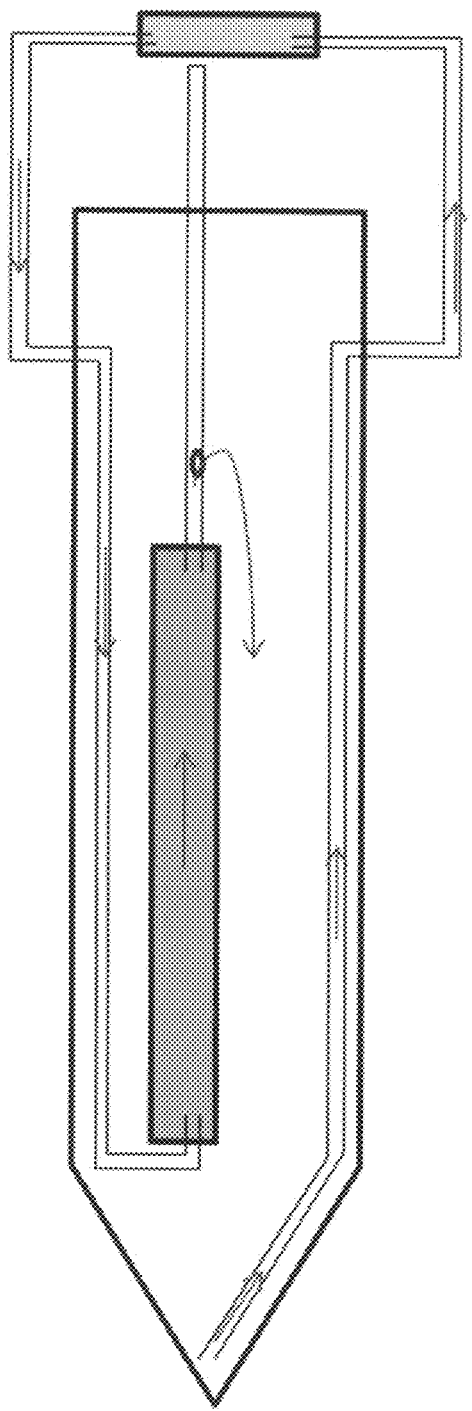
FIG. 6 shows a schematic of the bioreactor. The vessel is in the center of the chamber, and media is supplied through the pipes as shown. The direction of arrows indicates the flow of solutions in the pipes.
Figure 9B:
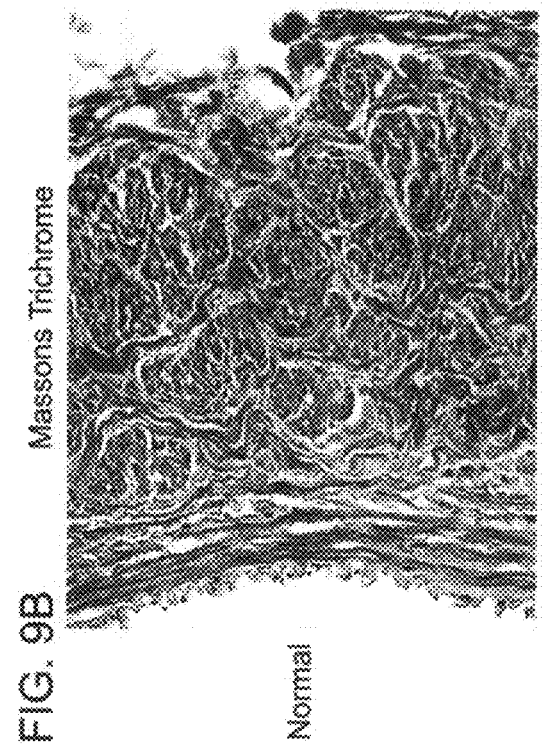
FIGS. 9A-9D show histological analysis by Massons Trichrome (MT) staining of normal veins (top panels, A-B) and decellularized veins (DC, bottom panels, C-D). No staining for nuclei was observed after 9 cycles of decellularization. MT staining also showed the preservation of collagen in decellularized veins.
Figure 9D:
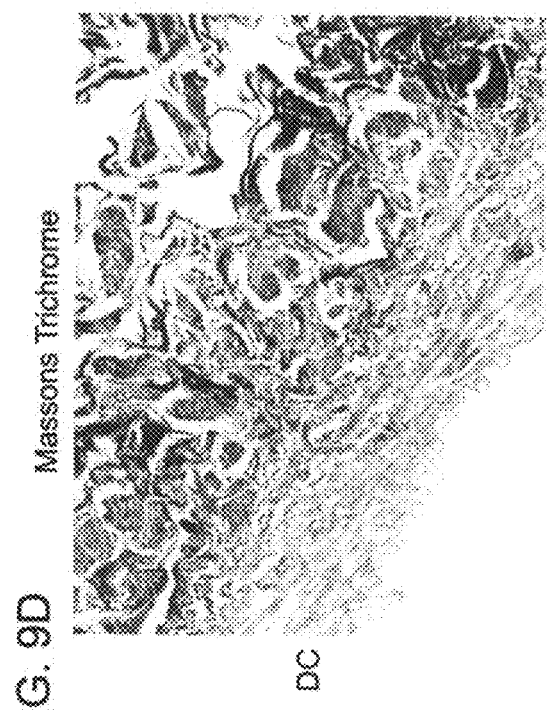
Figure 9A:
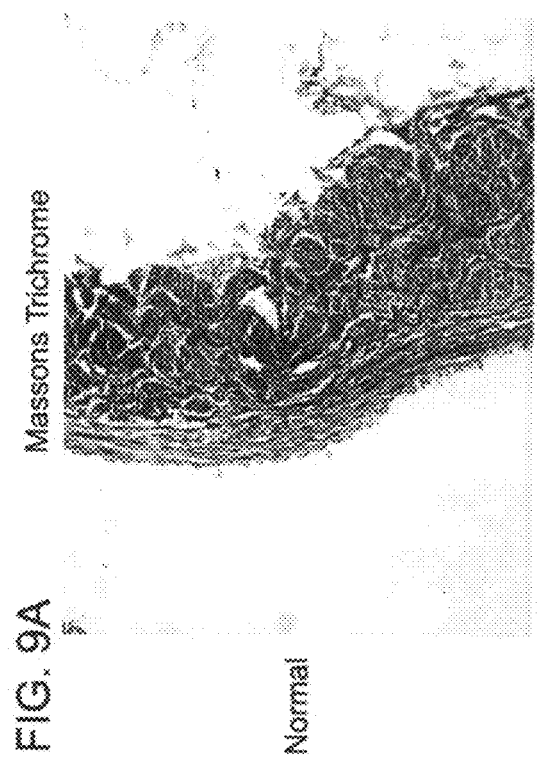
Figure 9C:
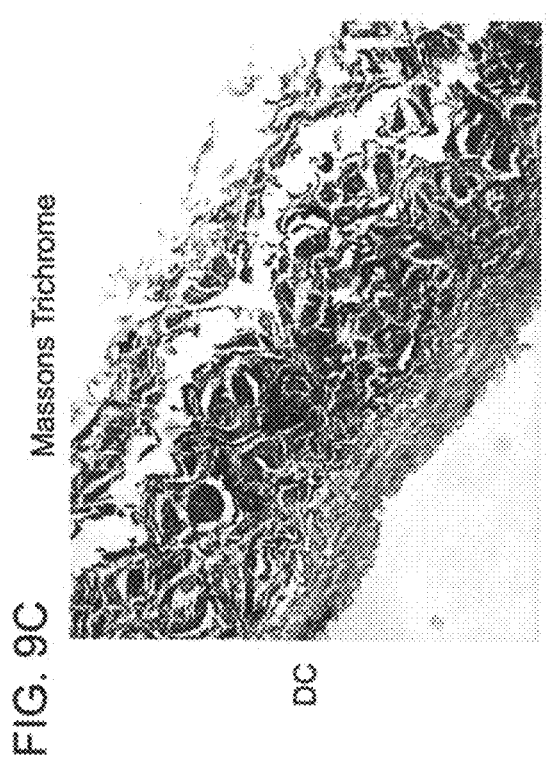
Figure 12A:
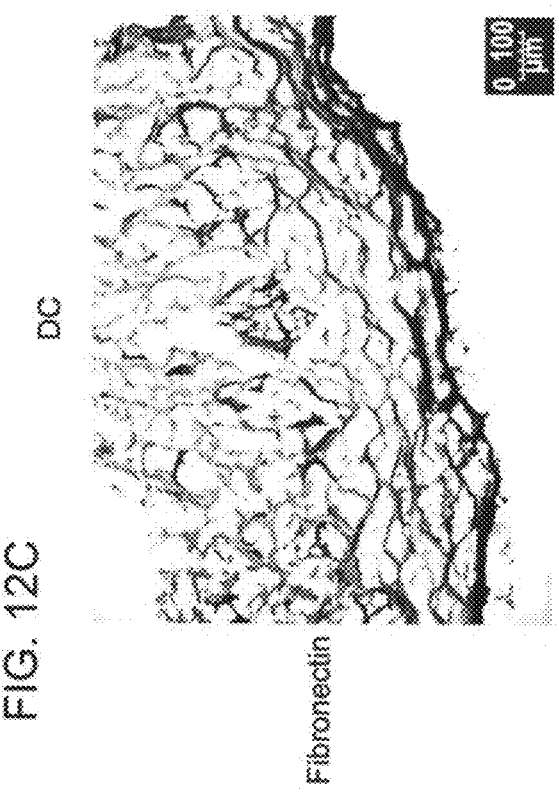
FIGS. 12A-12D show histological analysis by Vernhoeff Von Gieson (VVG) staining of normal veins (left panels, A-B) and decellularized veins (DC, right panels, C-D). VVG staining showed the preservation of fibronectin (top panels, A, C) and laminin (bottom panels, B, D) in decellularized veins.
Figure 12B:
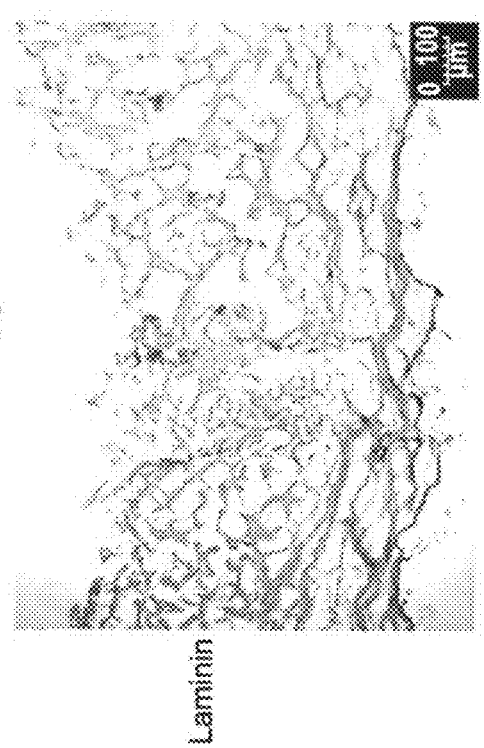
Figure 12C:
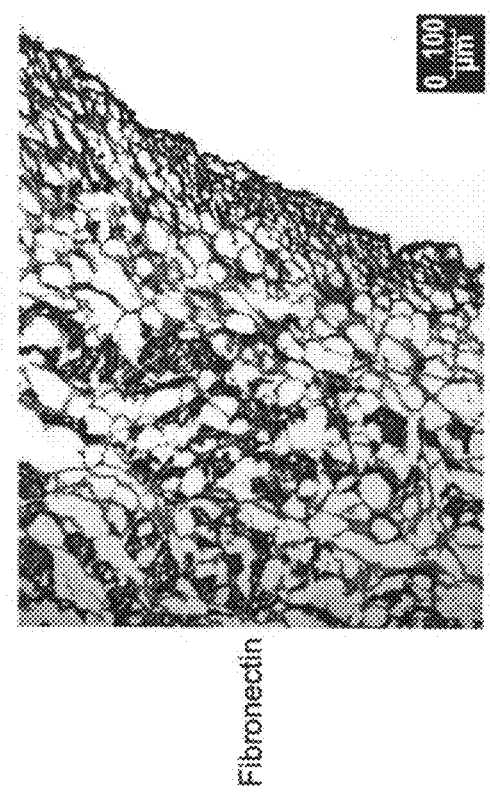
Figure 12D:
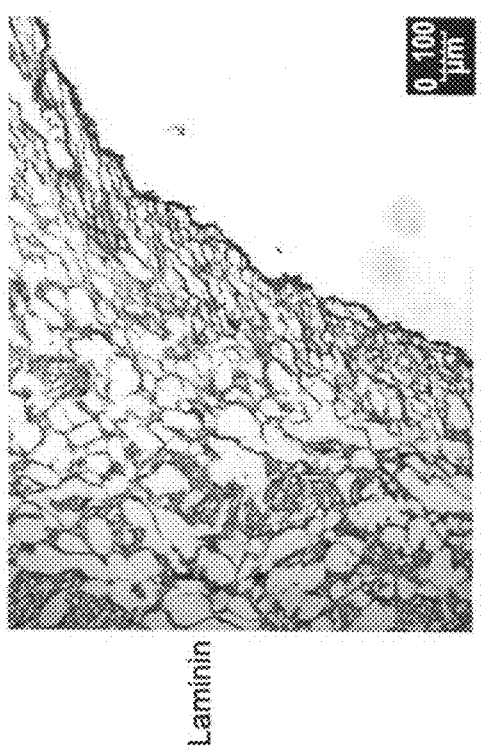

The present invention also provides for a bioreactor for recellularizing a blood vessel under the appropriate conditions, as described herein. Specifically, the bioreactor comprises a completely closed chamber that is large enough to fit the blood vessel to be recellularized and can be sterilized, a tube for supplying cells and/or media connected to a pumping mechanism (i.e., a peristaltic pump), a structure to which one end of the vessel is connected to, and 2 inlets and 2 outlets. The set-up of the tubes in relation to the blood vessel and pump allows the cells or media to flow through the lumen of the blood vessel, and flow around, or immerse, the exterior of the blood vessel. A schematic diagram depicting the set-up of an exemplary bioreactor is shown in FIG. 6.

In some instances, a blood vessel generated by the methods described herein is to be transplanted into a patient. In those cases, the cells used to recellularize a decellularized blood vessel can be obtained from the patient such that the regenerative cells are "autologous" to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue can be syngeneic (i.e., from an identical twin) to the patient, the cells can be human lymphocyte antigen (HLA)-matched cells from, for example, a relative of the patient or an HLA-matched individual unrelated to the patient, or cells can be allogeneic to the patient from, for example, a non-HLA-matched donor.

The progress of the seeded cells can be monitored during recellularization. For example, the number of cells on or in the decellularized blood vessel or tissue can be evaluated by taking a biopsy at one or more time points during recellularization. In addition, the amount of differentiation that the cells have undergone can be monitored by determining whether or not various markers are present in a cell or a population of cells. Markers associated with different cells types and different stages of differentiation for those cell types are known in the art, and can be readily detected using antibodies and standard immunoassays, immunofluorescence, immunohistochemistry or histology techniques. For example, to confirm the presence of endothelial cells, or cells that have differentiated in the endothetlial lineage, any endothelial markers known in the art can be assayed. Preferred endothelial markers include, but are not limited to CD31, VWR, VE-cadherin and AcLDL. For example, to confirm the presence of smooth muscle cells, or cells that have differentiated in the smooth muscle cell lineage, any smooth muscle cell markers known in the art can be assayed. Preferred smooth muscle cell markers include, but are not limited to smooth muscle actin and vimentin. Recellularization is achieved upon appropriate expression of at least one endothelial marker on the surface of the engineered vessel and at least one smooth muscle markers in the lumen of the engineered vessel.

In some embodiments, tensile strength of the engineered vessel may be tested. Tensile strength tests are known in the art. For example, an engineered vessel may be cut laterally into ring segments and tested by radial deformation. Total force used to break the samples completely and elongation at 50% total force can be calculated to determine tensile strength. In some embodiments, the recellularized vessels demonstrate increased tensile strengths when compared to decellularized vessels. For example, engineered blood vessels of the present invention may demonstrate the ability to withstand 10%, 20%, 30%, 40%, 50%, 60%, 70%, 80%, 90%, 100% or more total force in comparison to decellularized blood vessels. In other embodiments, the recellularized vessels demonstrate similar, or about the same tensile strength as normal vessels.

EXAMPLES

Example 1

Bioengineered Blood Vessel Using Bone Marrow

This Example describes the meso Rex procedure using a decellularized donor vein, recellularized with autologous stem cells, in a ten year old girl with EHPVO.

Extra-Hepatic Portal Vein Obstruction (EHPVO) is a condition with impaired hepato-pedal blood flow from the Superior-Mesenteric Vein (SMV), Splenic Vein (SV), Coronary Veins (CV) through the Portal Vein (PV).

Methods

A one year old girl was discovered to have thrombocytopenia and splenomegaly. She was thought to have idiopathic thrombocytopenic purpura (ITP) and was followed for several years at a local hospital. When she was 9.5 years old she was further investigated and esophageal varicose veins and splenomegaly were confirmed. INR was slightly elevated. Protein-S and Protein-C showed normal levels, and APC-resistance was excluded. She was medicated with betablockers to reduce the portal hypertension.

Elastography (Fibroscan®) was normal (stiffness core 4.6). A CT-angiography revealed a portal vein thrombosis with collateral circulation in the hepatic ligament and an open superior mesenteric vein (SMV) (FIG. 1A). Treatment with beta-blockers and proton pump inhibitors was initiated. Due to the portal hypertension and evolving esophageal varicose veins she was evaluated and accepted for a by-pass procedure (meso Rex). In case the umbilical vein should not be patent, an autologous stem cell derived vein graft was planned as a rescue procedure. The alternative would be either to use another vessel from the patient or from an allogeneic donor, or to perform a liver transplantation, the latter two requiring life-long immunosuppression. The internal jugular veins were patent on both sides (ultrasound and CT), but the estimated length of the graft was shorter than the distance from the left portal vein to the SMV. The intrahepatic portal vascular bed was difficult to visualize. This might be caused by the almost 9 years of EHPVO.

Decellularization of Donor Vein

A 9 cm vein segment was retrieved from a healthy 30 year old organ transplant donor who had no ongoing infections or other diseases. One end of the vein was kept open, while the rest of the openings were sutured to prevent leakage. The vein was rinsed in phosphate buffered saline (PBS) containing 0.5% penicillin, 0.5% streptomycin, and 0.5%% amphotericin B. Initially, the tissue was rinsed in distilled water (D/W) for 72 h. Each decellularization cycle consisted of incubation with 1% Triton™ X (3 hrs), followed by 1% Tri n Butyl Phosphate (3 hrs) and 0.004 mg/ml deoxyribonuclease I (all Sigma, Gothenburg, Sweden) in 1 M sodium chloride (3 hrs). One end of the graft was kept open while the other was clamped and the lumen was filled with 1% Triton™ X (Sigma, Gothenburg, Sweden). The other end was then clamped and placed on an agitator at 37° C. for 3 h with gentle shaking. At the end of the incubation time, one end of the specimen was opened, the contents of the lumen were emptied and the specimen was washed with PBS. The same procedure was followed for treatment with Tri n Butyl Phosphate (Sigma), and DNAse (Sigma). Lastly, the specimen was washed with distilled water overnight to remove cell debris. Seven cycles were run. At the end of the decellularization process, the graft was washed continuously for 48 hrs with PBS (changed every 6 hrs). All solutions used for decellularization contained the above mentioned antibiotics. After each cycle a small piece of tissue was screened for the presence of nuclei, HLA class I and II antigens and verified histologically using standard procedure.

Preparation of Recipient's Autologous Endothelial and Smooth Muscle Cells

Autologous recipient cells were prepared from 20 ml of bone-marrow obtained from the recipient. The bone-marrow was first separated on lymphoprep and washed three times with Dulbecco's modified eagle medium (DMEM). Endothelial cells were isolated with CD133-coated Mini MACS™ beads according to the manufacturer's instructions. The number of CD133+ cells obtained was counted and viability tested using trypan blue. CD133+ cells were cultured in 0.2% gelatine coated culture wells at 37° C. in a humidified atmosphere of 95% air and 5% $CO_2$. For preparation of complete media: basal medium MCDB 131+10% heat inactivated human AB serum, 1% L-glutamine and 1% penicillin-streptomycin+ supplemented with EGM™-2 Single Quote kit (Lonza, Walkersville, MD USA) containing ascorbic acid, hydrocortisone, transferrin, insulin, recombinant human vascular endothelial growth factor, human fibroblast growth factor, human epithelial growth factor, heparin and gentamicin sulfate. The medium was replaced every 2-3 days. Confluent cells from all wells were detached by trypsinization, pooled and washed once with phosphate buffered saline (PBS). Cultured autologous recipient endothelial cells at first passage were stained with dual-color immunofluorescence for VE cadherin, Acetylated LDL and von Willebrand factor, counterstained with 4',6-diamidino-2-phenylindole (DAPI) to confirm endothelial phenotype before attachment to the matrix in the bioreactor.

For smooth muscle cells, the cells isolated from bonemarrow were grown in commercially available smooth muscle cell medium (Cascade Biologics–medium 231+ growth factor supplements cat. no. S-007-25). Cells were counted and seeded in 75 $cm^2$ flasks at a density of $1\times10^6$ per mL. Cells were grown in complete medium and the medium was replaced every 3 days. When cells reached 90% confluence, the supernatant was removed and the cells washed with PBS and then passaged with 1× trypsin-EDTA. To induce smooth muscle differentiation, the culture medium was changed to complete medium containing smooth muscle cell differentiation supplement (Cascade Biologics–cat. no. S-008-5). Cultured autologous recipient smooth muscle cells were stained with immunofluorescence histology for alpha actin and vimentin counterstained with DAPI to confirm smooth muscle cell phenotype before attachment to the matrix in the bioreactor.

Seeding of Cells

Endothelial cells were detached from culture flasks, diluted in their growth specific medium, and applied longitudinally to the internal surface of the matrix with a micro syringe. The mean number of seeded EC per square centimeter of graft surface was $7.5\times10^4$. The open end was clamped and the matrix was placed on a rock'n roller at 37° C. with 5% $CO_2$. After 3 days, the internal surface was seeded with the same density of smooth muscle cells suspended in smooth muscle cell differentiation medium and further incubated for 3 days. The matrix was then placed within a bioreactor. Endothelial cell medium without serum (serum-free medium) was added internally (25 ml) and serum-free SMC differentiation medium externally (25 ml) and rotation started at 1.5 revolutions per min (37° C., 5% $CO_2$). The external and internal medium was changed every 72 hrs. The extracted medium was tested for microbial colonization using a commercially available kit (Invitrogen, Sweden, cat. No. C-7028). The total period of bioreactor culture was two weeks.

Surgical Procedure

The operation was planned to a date when the vein graft was ready. It was transferred to cold storage solution from the bioreactor at the time of surgery. The patient was opened with a Mercedes like incision to expose the hepatic ligament and hilum. The round ligament was mobilized carefully from the umbilicus to the liver. The umbilical vein was found and was very small and only partly patent. Varicose veins in the left part of the abdomen were found and the enlarged spleen filled the left hypocondrium. The varicose veins were of poor quality and not suitable for bypass. The preoperative length of the jugular vein was not explored due to estimated too short length for the bypass.

Dissection of the hilum was commenced, following the round ligament down to the left portal vein which was found patent. The extra-hepatic right portal vein was thin and a common portal vein above pancreas was not found. Further dissection of the left portal vein included opening of the umbilical vein at the junction. A fibrous ligament was found that could be removed with dilatation, revealing a good left portal vein with good backflow. The lumen was dilated to 15 mm. The right portal vein was not identified and small branches from segment three to segment four were seen.

The next step included finding the superior mesenteric vein (SMV). The Treitz ligament was identified and the duodenum was mobilized to expose the inferior mesenteric vein. By following this vein, the splenic vein and the SMV could easily be mobilized. The SMV was patent and enlarged.

The decision to use the stem cell derived vein was taken because of no good alternative using the child's own veins without extensive additional surgery using a combination of jugular, iliacal or saphenous veins. Without bypass, liver or multivisceral transplantation would be the option.

The stem cell seeded vein was brought into the operating room. A suitable length of the Y shaped graft was selected and prepared for bypass. The anastomosis to the SMV was first carried out by clamping the SMV after mobilization. The graft was sutured with 5-0 Surgipro® end to side and the clamp was then released with a vascular clamp on the graft (FIG. 1B). The graft was placed over the pancreas but under the colon and stomach. The vascular clamp was moved in steps to reassure a graft without leaks. Next, a clamp was put on the intrahepatic left portal vein and the graft was anastomosed to the portal vein (FIG. 1C). The graft was larger than the portal vein, but by adjusting the sutures this was overcome.

Postoperative Monitoring

Figure 1E:
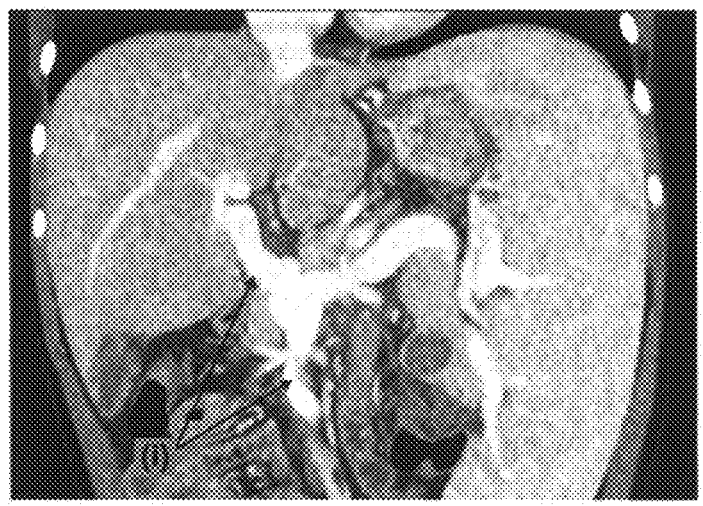

Reperfusion was uneventful. Good blood flows of 25-30 cm/s in the portal vein and 40 cm/s in the artery were measured intra-operatively and confirmed with ultrasound (FIG. 1D). Intraoperative portal vein pressure was 20 mm Hg at the start of the procedure, but was not measured after reperfusion of the portal vein. The patient was followed with ultrasound twice daily the first week and then daily during the second week. Blood flows reached up to 80 cm/s in some left portal branches, while lower flows of 15 cm/s were seen in the right portal vein. The graft was visualized using CT Angiography one week after surgery and found to be patent (FIG. 1E). A postoperative ultrasound noticed a changed contour of the vessel wall at the site of the portal anastomosis on postoperative day seven and the radiologist could not rule out a thrombosis at this site. Hence, postoperatively the patient was put on Heparin® 1000IE 6 times daily intravenously and followed with ultrasound twice daily to monitor this finding. After a few days, the patient had a bleeding from the wound dressing and a fall in hemoglobin, but did not need blood transfusion. The APTT was found to be >210 the same day, probably caused by the heparin treatment, and therefore temporarily stopped. The patient was monitored continuously for the first month, with sequential blood tests for donor antigens, liver enzymes and imaging of blood flow speed using ultrasound were performed. Similar tests were performed at 3, 6, 9, and 12 months post-transplant.

Anti-Endothelial Cell Antibody Screening

Screening for anti-endothelial cell antibodies was performed both pre and post transplantation. Serum samples were collected one month prior to 1 and 3 weeks, 1, 3, 6, 9 and 12 months post-transplantation. On each occasion, peripheral blood mononuclear cells (PBMC) expressing the angiopoietin receptor Tie-2 were freshly isolated from blood samples of the patient using the commercial XM-ONE® kit according to the instructions of the manufacturer (AbSorber AB, Stockholm, Sweden). The cells were analyzed immediately on Guava® flow cytometer (Millipore, Gothenburg, Sweden) using Guava® analysis software. Serum from a healthy non-transfused blood group AB male known not to have any antibodies served as negative control. A pool of sera from patients who had formed alloantibodies as a result of multiple blood transfusions or organ transplantations was used as positive control. Frozen lymphocytes from the cadaveric donor were also used as targets for screening of anti-donor HLA antibodies and anti-endothelial cell antibodies as described above.

Results

Figure 2B:
FIGS. 2A-2J show the macroscopic and microscopic view of iliac vein before and after decellularization. (A) Original blood vessels obtained from a deceased donor. Hematoxylin and eosin staining of iliac vein shows presence of nuclei (blue) in the native graft (B) and the presence of a clear endothelial layer. Immunohistochemistry of the same vein showing presence of MHC class I (C; black brown staining) but no MHC class II (D) since EC and SMC do not constitutively express MHC class II). (E) A translucent iliac vein after 7 cycles of detergent-enzymatic treatment. Although the decellularized tissue maintained structural integrity, the absence of blue-stained cell nuclei (F), MHC class I (G) and MHC class II (H) indicates that the luminal surface as well as the matrix are completely acellular. Flow cytometric analysis was performed to detect anti-endothelial cell antibodies using the XM-ONE kit. Representative histograms demonstrating the absence of binding of anti-endothelial cell antibodies (I), while a positive reaction was obtained with the positive control serum (J). Black line represents negative control. Magnification for FIGS. 2B-2H 20×.
Figure 2D:
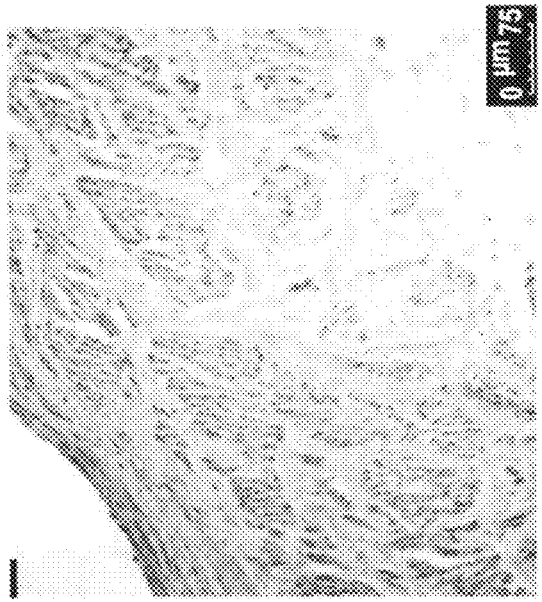
Figure 2A:
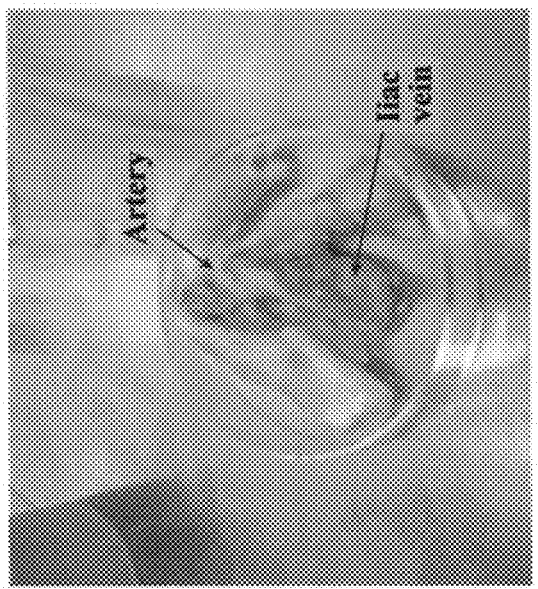
Figure 2C:
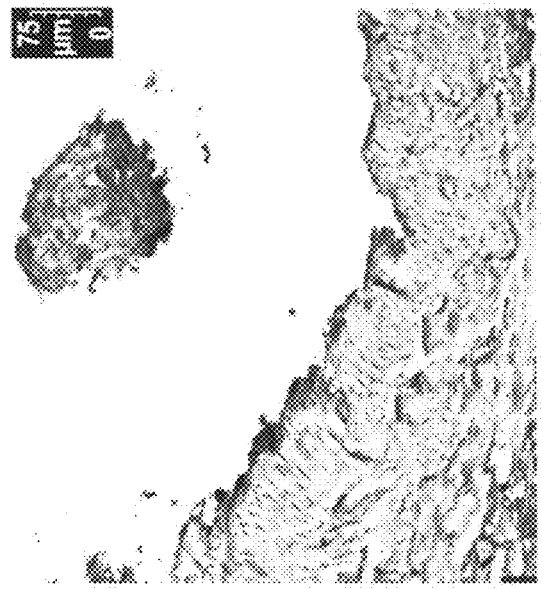
Figure 2F:
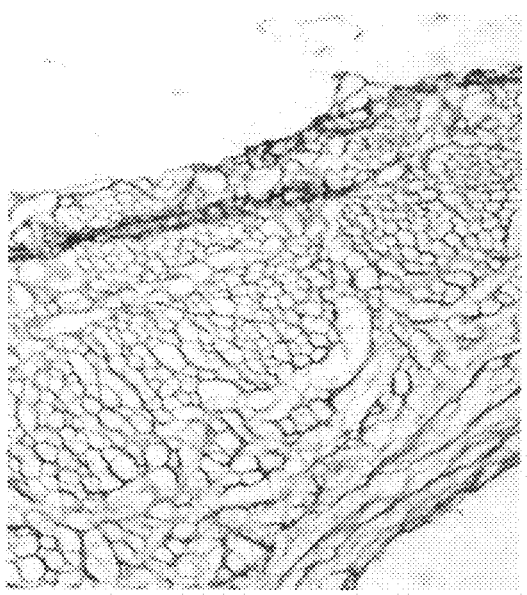
Figure 2H:
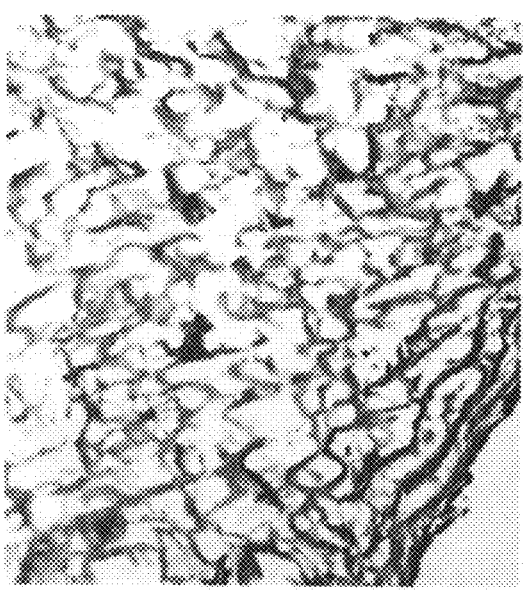
Figure 2E:
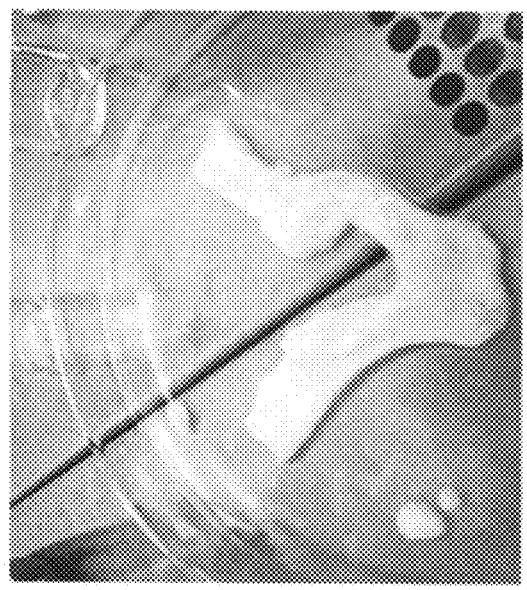
Figure 2G:
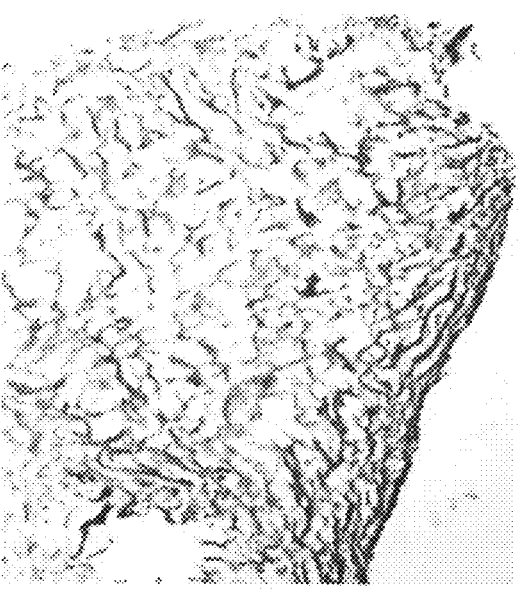

Using Triton™, TnBP and Dnase, the donor vein was successfully decellularized after seven cycles. The gross morphology of the iliac vein before and after decellularization is shown in FIGS. 2A-2H. The architecture of the decellularized vein was however different from the native control (FIG. 2B). No nuclei or expression of HLA class I or II antigens on the decellularized vein graft was found at the end of cycle 7 (FIGS. 2F-2H). The entire decellularization procedure took 12 days; at the end of which it was found that the vein was successfully decellularized (based on histological findings). Isolated CD133+stem cells from the bone-marrow of the patient differentiated very easily into mature endothelial cells expressing VE-cadherin (FIG. 3A), AcLDL (FIG. 3C) and vWF (FIG. 3D). Similarly, smooth muscle cells could be successfully grown from bone-marrow cells, which later differentiated into cells expressing alpha-smooth actin (FIG. 3B) and vimentin (FIG. 3E). The total time for isolation and expansion of EC and SMC was approximately 15 days.

Figure 4A:
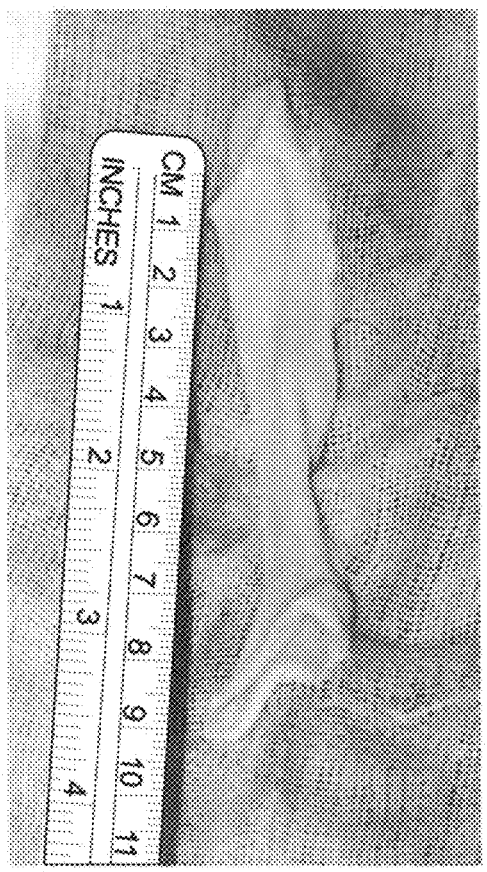
FIGS. 4A-4J show the macroscopic and microscopic view of the bioengineered vein grafts. Gross photographs of the two bioengineered vein grafts (A-graft 1) and (B-graft 2). C&D negative controls for immunohistochemistry and immunofluorescence. After two weeks of seeding incubation with recipient's stem cells, the grafts were completely recellularized (E-J) as evidenced by a confluent EC monolayer on the vessel wall and presence of smooth muscle cells in the media. IHC staining (brown) of paraffin sections from graft 1showing the clear presence of endothelial cells covering 90% of the lumen (E) and the valves (F). (G) Presence of smooth muscles cells is also visible in the media. IF staining of graft 2 showed similar results. EC are detected (green) in the lumen (H) and valves (I), and SMC (red) (J) in the media. Magnification 20×.
Figure 4B:
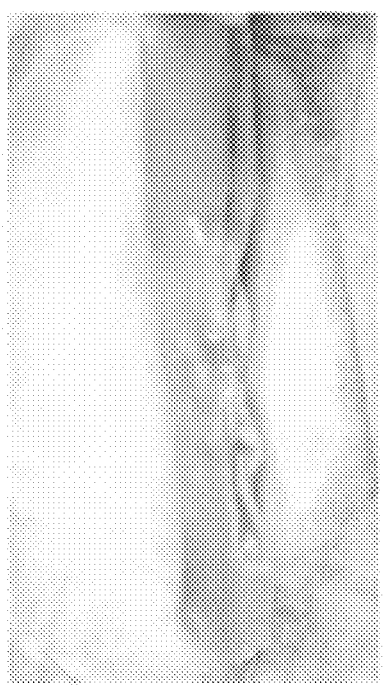
Figure 4C:
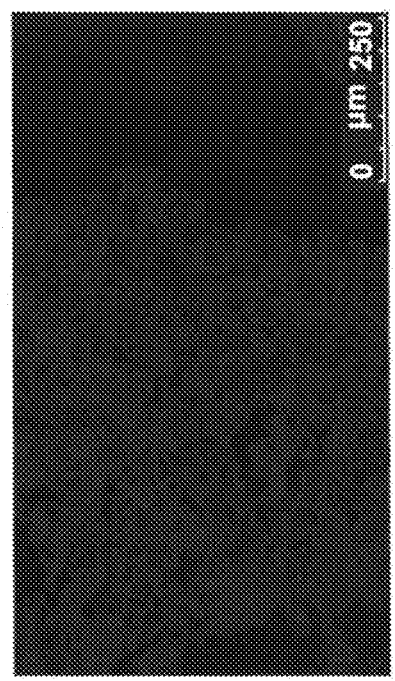

Both cell types in passage 4 were used for recellularization of the vein graft. Gross pictures of the two grafts used are shown in FIGS. 4A-4B. All cells were characterized once again immediately prior to seeding and found to express the required phenotypic markers. In the recellularized vein, ECs were found in the lumen, while SMC had migrated into the walls of the tissue as detected by immunohistochemistry and immunofluorescence (FIGS. 4C-4J). Moreover, both cell types expressed their specific markers after culture in the bioreactor (FIGS. 4E-4H). As seen in this figure, approximately 80-90% of the lumen was found to be covered by an endothelial layer prior to implantation in the patient. It was also found that most of the valves in the graft were re-endothelialized (FIGS. 4E and 4H). Based on these results, it was decided to proceed to transplantation. The total time for preparation of the graft for transplantation after bone-marrow aspiration including culture in the bioreactor was approximately one month.

Figure 2I:
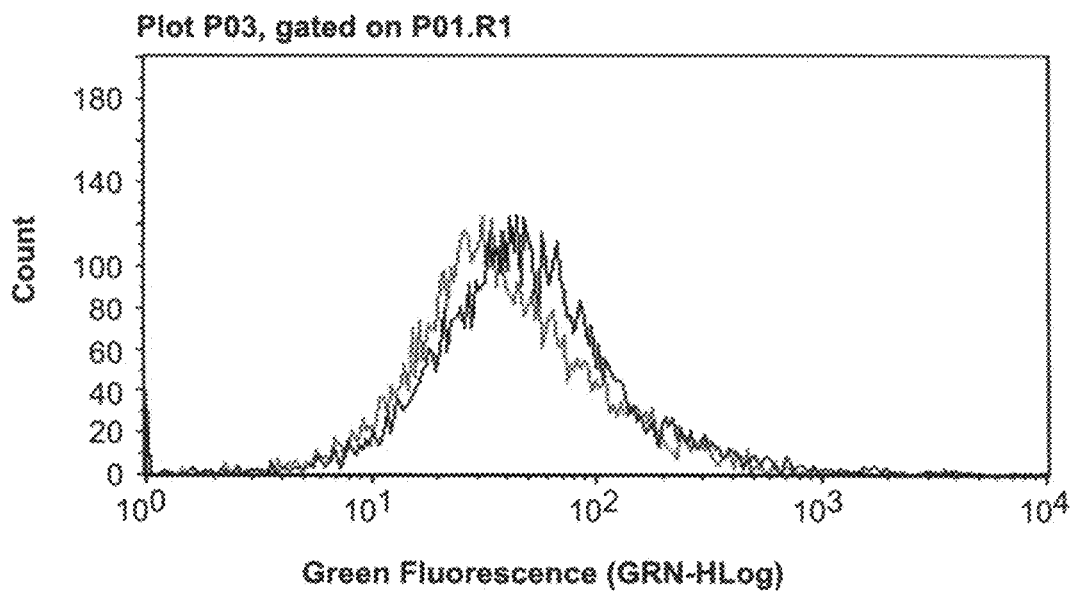
Figure 2J:
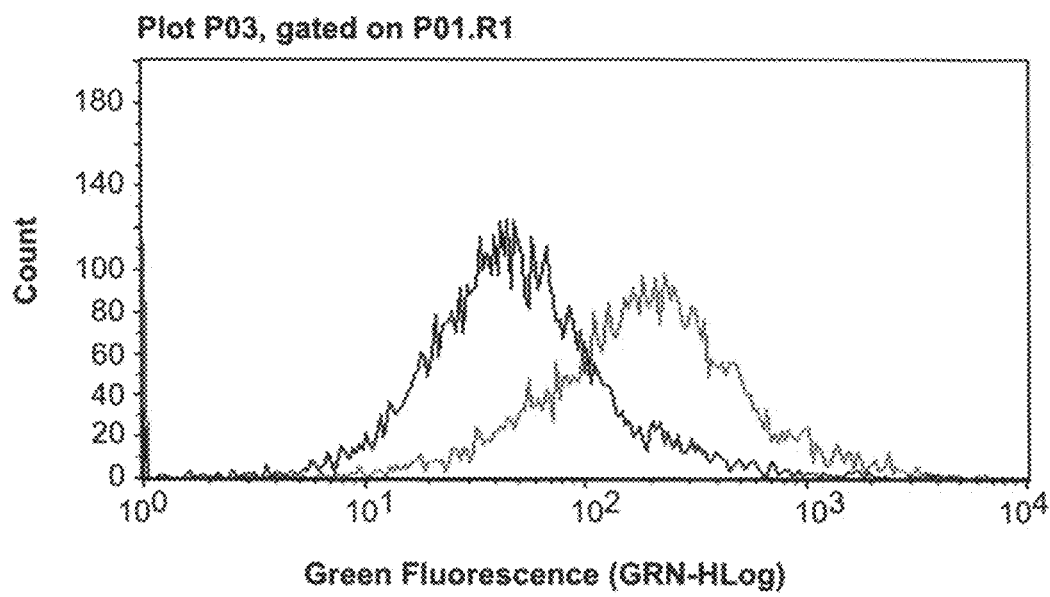
Figure 5A:
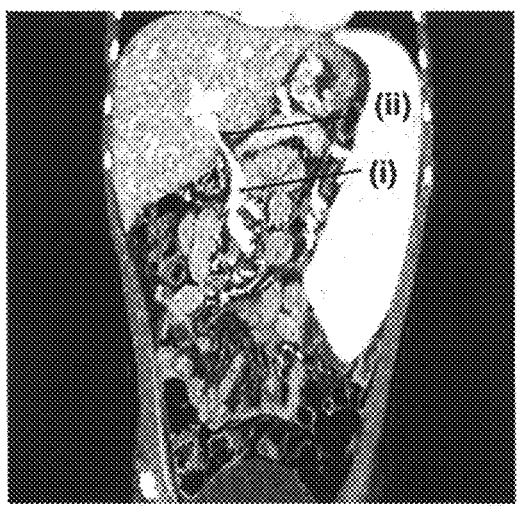
FIGS. 5A-5G show pictures post-transplant. (A) The image shows that one year post-transplant, the graft (graft 1) was narrowed at the portal vein but was patent. The image has been reconstructed using 3-4 images to visualize the entire length of the graft. The diameter of the vein at the SMV (i) is 6 mm and closer to the left portal vein (ii) 4 mm (B) The primary graft is shown at the site of the SMV anastomosis (i). The vessel is thin walled and patent. (C) The primary graft close to the left portal anastomosis (ii), showing a narrowed graft partially strictured by tissue from the meso-colon. Therefore surgical correction of the meso-Rex shunt was done using a second stem-cell derived vein graft. (D) The image shows completion of the left portal vein anastomosis after dissection of the portal vein further into the liver using an ultra-sound dissector (CUSA) and releasing the tissue causing the stricture in the meso-colon (iii). (E) Image showing completion of the distal anastomosis by patching the new graft to the old SMV anastomosis. After 24 hours this was revised and the anastomosis enlarged after extending the opening of the SMV. (F) Ultrasound images demonstrating restituted blood flow of over 20 cm/s in the graft (G) and a good intra-hepatic portal vein blood flow of 25-40 cm/s.

The patient was discharged 3 weeks after the procedure with normal liver function tests (LFT) except the INR (1.4). She responded more quickly and was more alert than prior to transplantation. At 4.5 weeks follow-up the patient had normal liver values including INR (1.2), which had improved from 1.4 pre-operatively. She was markedly less tired and an improved life quality was reported by the parents. At the 3 and 6 month check-up the patient was doing fine with a patent graft on ultrasound and normal laboratory tests. There was no detection of any anti-endothelial cell antibodies pre and/or post-transplantation (FIGS. 2I, 2J). After the 6 month check-up, the patient was more tired; however the laboratory tests were normal, except for a decreased platelet count. A CT angiography, performed after the visit, showed that the lumen had decreased from 8 mm to 4-6 mm (FIG. 5A). An ultrasound confirmed a decreased portal flow. A decision to explore the patient was taken after a thorough discussion with the pediatric team and the parents.

One year after the primary procedure, the patient was explored again. It was decided to if possible correct the narrowed graft or use an alternative autologous vein from the internal jugular on the left side. As a precaution, a new stem-cell derived vein as described earlier was prepared after acquiring the necessary permissions (see FIGS. 4B, 4H-4J).

Figure 5B:
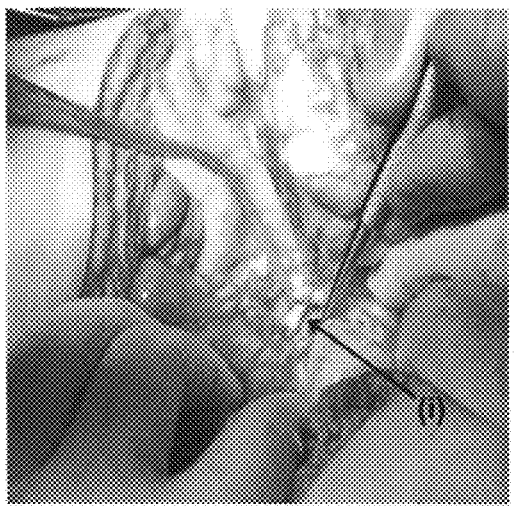
Figure 5C:
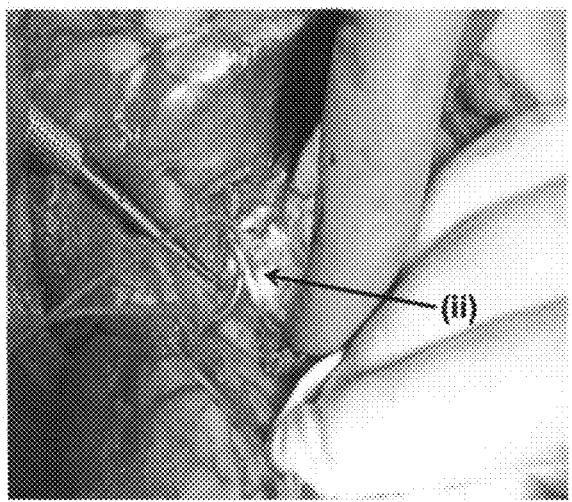
Figure 5D:
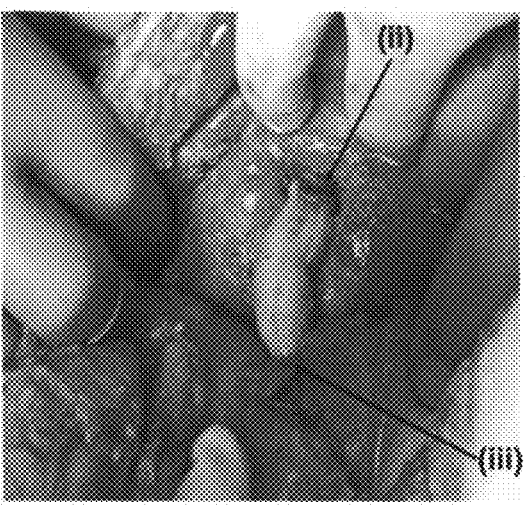
Figure 5E:
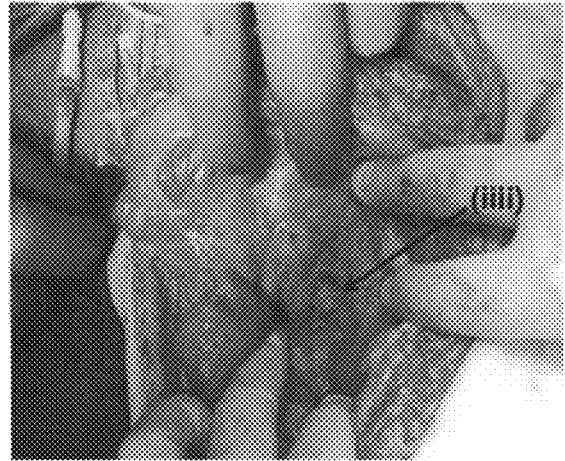
Figure 5F:
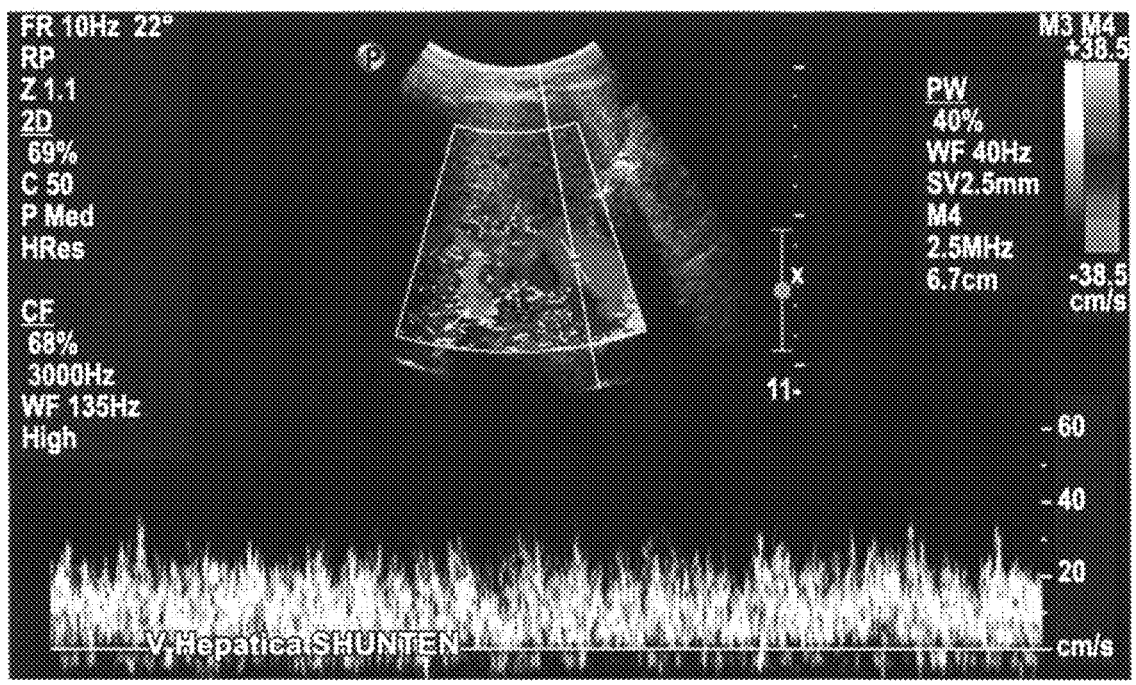
Figure 5G:
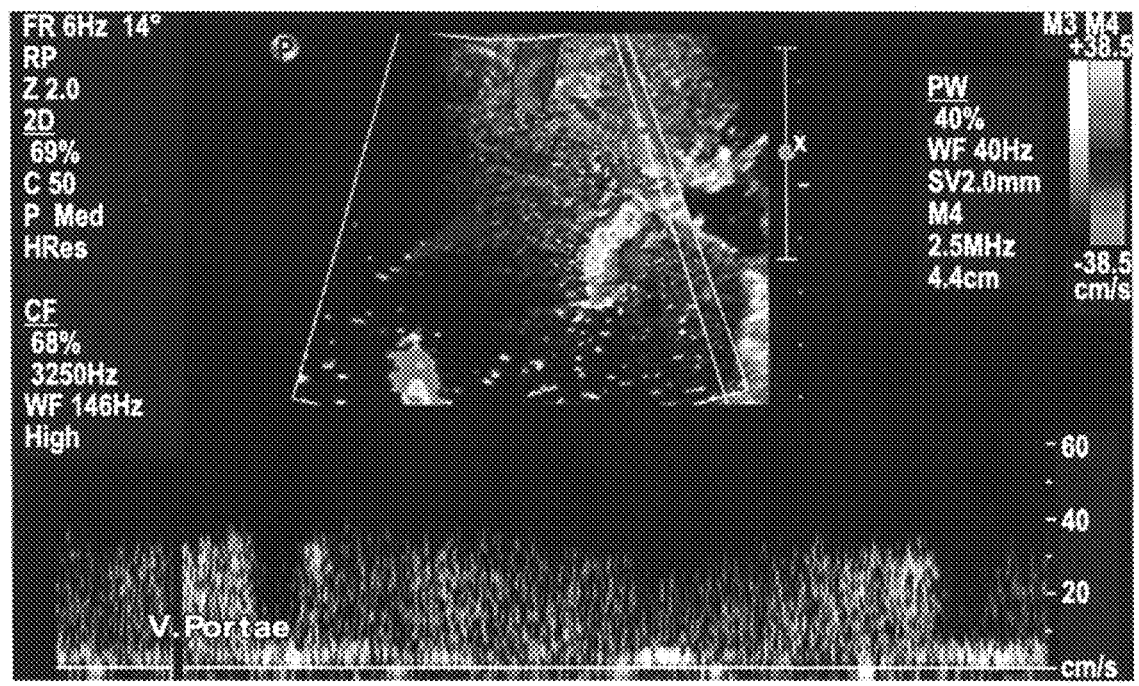

At the site of the anastomoses to the SMV, a patent graft with a diameter of 8*mm* was found (FIG. 5B). The graft was compressed at the site of the passage through the mesocolon, to allow the vessel "to hang" on the tissue behind the graft. The remaining part of the graft to the left portal vein was narrowed to 4-6 mm in diameter but patent (FIG. 5C). The graft looked normal with thin walls. A thickening of the retro-peritoneum at the site of SMV was detected, as noted one year earlier in the surgical notes of the primary procedure. Once the tissue causing the compression of the vessel was removed the graft dilated further, but due to the shortening of the graft close to the left portal anastomosis, the best solution was to place a new vein at this site and explore the anastomosis at the same time. The internal jugular vein was judged as being too short. So the decision was taken to use the newly prepared stem-cells derived vein graft.

Figure 4D:
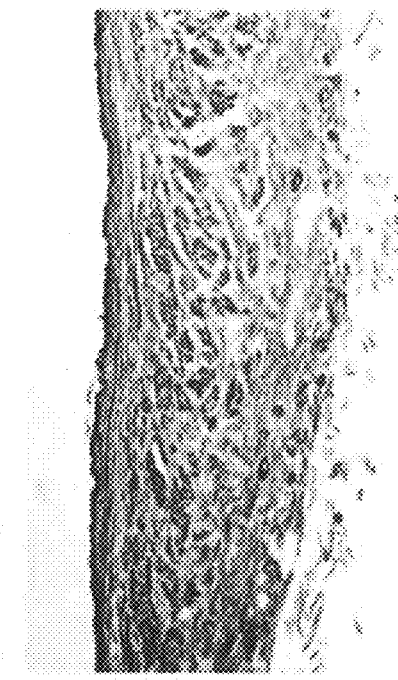
Figure 4E:
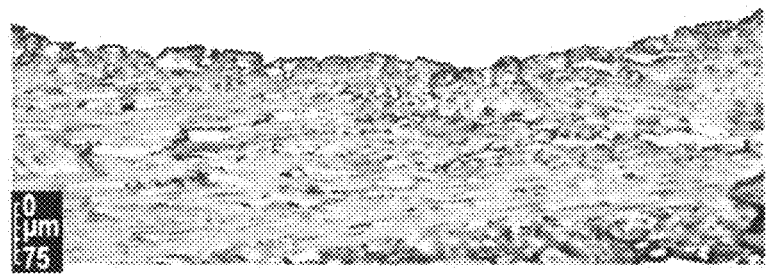
Figure 4F:
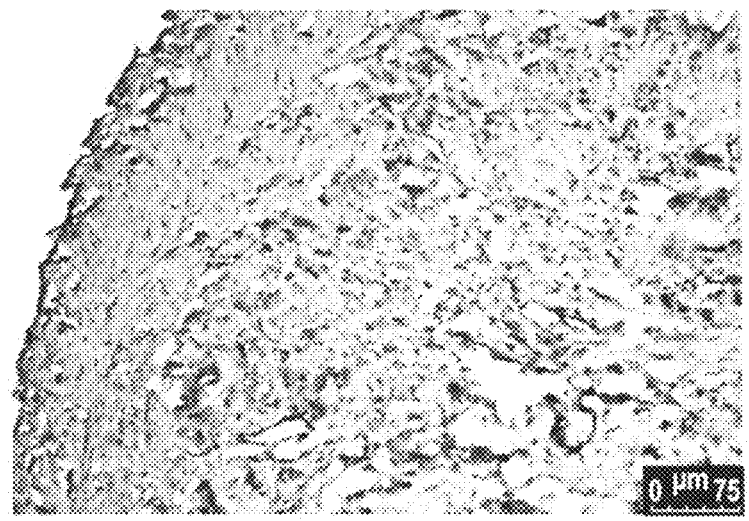
Figure 4G:
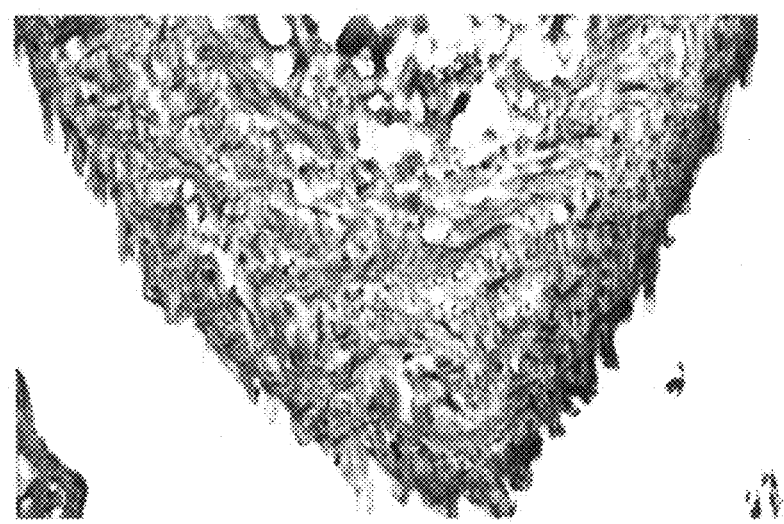
Figure 4H:
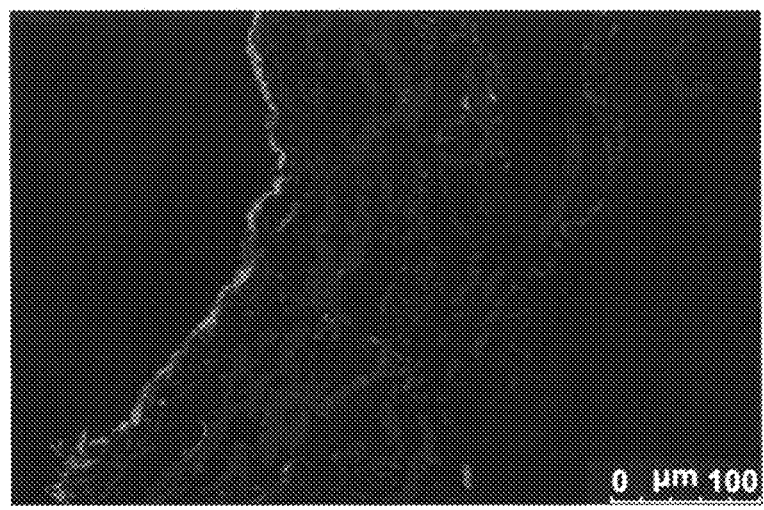
Figure 4I:
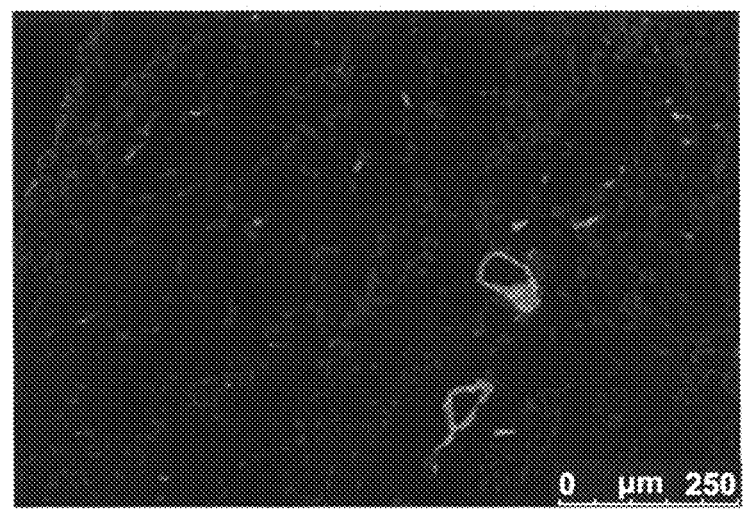
Figure 4J:
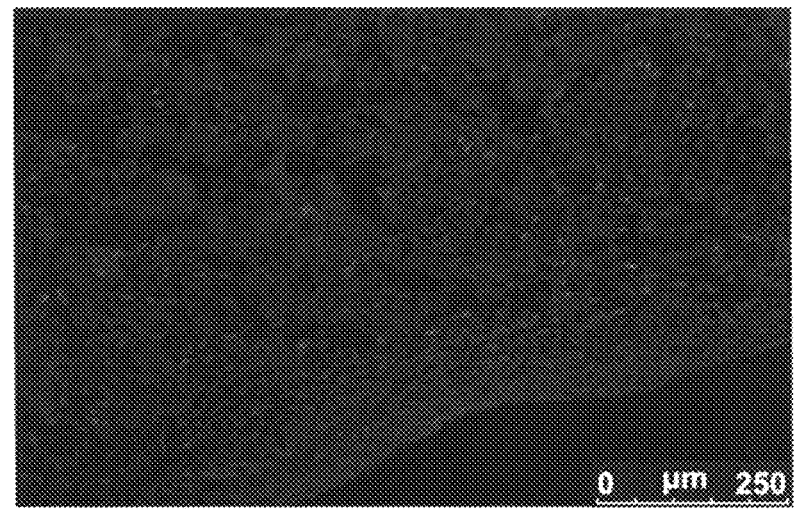

A new graft was placed from the hilum after dissecting the left portal vein even further into the liver, using an ultra sound dissector (CUSA) and patching the SMV anastomosis (FIGS. 4D-4E). Blood flows of over 20 cm/s in the graft and the portal vein could be registered per and postoperatively (FIGS. 4F-4G). The patient was explored 24 hours after surgery due to a reduced blood flow. The distal anastomosis to the SMV had a clot, and was redone. Portal pressure was 20 mm Hg before surgery and 13 mm Hg after reperfusion of the graft. Collaterals along the minor and major curvature of the stomach were ligated before closing the patient. The patient did not receive any immunosuppressive drugs, but received 75 mg of salicylic acid once daily and 10 mg omeprazole for 6 months after the primary operation. The betablocker was withdrawn on the day of surgery. After the second operation, the patient was put on intravenous heparin for 2 weeks, and is administered anticoagulants for 6-12 months after the procedure.

The patient has shown improvement in both height and weight and has grown in one year from 137 cm to 142.5 cm and increased in weight from 30.2 kg to 35 kg.

Discussion

These results demonstrated successful recellularization of a decellularized human iliac vein using autologous stem cells, which was subsequently used for a by-pass procedure between the superior mesenteric vein and the intrahepatic left portal vein in a patient with portal vein thrombosis.

The histology results showed that decellularization with Triton™-X-TnBP and DNase is complete and allows the adequate preservation of the extracellular matrix. Already after 4 cycles, human veins can be decellularized with remnants of nuclei. It was also found that use of Triton™-X-TnBP instead of Na-deoxycholate retained a much better extracellular matrix such as elastin and fibronectin. Thus, a decellularization protocol was successfully applied to human venous tissue as verified by the absence of donor cells.

It was postulated that in vitro migration of smooth muscle cells into the media would be facilitated in the presence of an intact endothelium. Therefore, first, the endothelial cells were seeded which formed a layer on the graft within 3 days. After this the smooth muscle cells were seeded into the lumen of the vein and these cells were found to embed after 24 hrs. However, the complete recellularization of the vein took a total of 2 weeks. No external seeding of SMC was performed since it was found that the approach had successfully repopulated the media of the vein with SMC. Although re-seeding of the decellularized vein was not performed using perfusion, this is important. It is known that shear stress is required for optimal EC lining in the lumen. Use of perfusion recellularization for blood vessels is developed.

The data presented proof of concept that allogeneic human tissues from deceased donors can be reengineered using autologous stem cells for successful "personalized" or tailor-made transplants. Furthermore new areas of research are developed which reproduces arteries for surgical use in patients with arterio-venous fistulas for dialysis or coronary by-pass surgery.

Example 2

Allogeneic Blood Vessel Using Whole Blood

Post natal vasculogenesis is the formation of new blood vessels in adult contributed by circulating endothelial progenitor cells (EPCs) and angiogenesis is formation of new blood vessels from pre-existing endothelial cells. These two processes contribute in formation of vessel branches and in pathogenic states like wound healing, ischaemia, fracture healing, tumor growth etc. There are endothelial cells and endothelial progenitor cells co-existing in circulation, and the endothelial progenitor cells contribute to vascularization. Furthermore, progenitor cells for smooth muscle cells-another important cell type in blood vessels, are also present in circulating blood.

A reliable and reproducible procedure was developed that is clinically feasible globally. Since circulating angiogenic cells are present in whole blood, use of whole blood for regeneration of vein resulted in efficient recellularization of blood vessels without the need to isolate and expand subpopulations of angiogenic progenitor cells from bone-marrow or whole blood.

In the current invention, 5 human iliac veins were decellularized by a combination of perfusion and agitation and then recellularized by perfusing with whole peripheral blood followed by perfusion with endothelial and smooth muscle cells growth media respectively. Successful recellularization process was confirmed by the presence of endothelial and smooth muscle cells and also mechanical properties. To test in vivo patency, two patients suffering with extra hepatic portal vein obstruction (EPHVO) were selected and a tissue engineered vein regenerated using autologous peripheral blood was transplanted. The patients are followed for 8 and 6 months. The results prove the clinical potential of this method in treatment for patients with vascular diseases.

Materials and Methods

Decellularization of Veins

Human iliac veins about 7-9 ems were retrieved from cadaveric organ donors, stored in sterile PBS with antibiotics and transported to laboratory. The veins were immediately washed with distilled water to remove whole blood. Both the ends of vein were connected to connector with lid and the other abrasions, branches were sutured preventing leakage. Decellularization cycle comprised agitation of veins with 1% Triton™-X 100 (×100, Sigma, Sweden), 1% tri-n-butyl phosphate (TNBP) (28726.291, VWR, Sweden) and 4 mg/L deoxyribonuclease I (DNase I) (D7291, Sigma, Sweden) for 4 h with each solution in an agitator at 160 RPM speed at 37° C. Triton™ and TNBP solutions were prepared in distilled water containing antibiotics penicillin 200 U/ml, Streptomycin 0.2 mg/ml and amphotericin 2 ug/ml) (Sweden), 5 mM ethylenediaminetetraaceticacid (EDTA) disodium salt dehydrate (ED2SS, Sigma, Sweden) and 0.4 mM phenyl methyl sulfonyl fluoride (PMSF) (93482, Sigma, Sweden). DNase I solution was prepared in Dulbecos PBS with calcium chloride and Magnesium chloride (A12858, Life technologies). Decellularization was continued for 9 cycles with washing in between each cycle by perfusion with distilled water. After decellularization, tissue was sterilized with 0.1% peracetic acid in sterile PBS for 1 h followed by washing with sterile distilled water and PBS for 24 h with each solution.

Characterization of Decellularized Veins

After 9 cycles, biopsies were taken from decellularized veins and processed for immunohistochemistry, immunofluorescence, DNA quantification, luminex, scanning and transmission electron microscopic analysis, tensile strength and extracellular matrix quantifications.

Histology, Immunohistochemistry and Immunofluorescence

Normal, decellularized and recellularized vein biopsies were processed following the same protocol. Biopsies were fixed in 4% buffered formalin for 48 h to prepare paraffin block and tissue tech OCT for cryoblock and frozen in liquid nitrogen. The paraffin and cryosections of 5um thickness were cut for stainings. The paraffin sections after rehydration in descending series of alcohols were stained with hematoxilin-eosin (HE), massons trichrome (MT), vernhoeff von gieson (VVG) staining and immunohistochemistry. In HE staining the slides were incubated in Meyers hematoxylin and alcoholic eosin for 7 and 1 min respectively, followed by washing with distilled water in between for 10 min, later dehydrated and mounted. The MT (25088-1, Polysciences, Germany) and VVG (25089-1, Polysciences, Germany) staining were performed according to the manufacturer's instructions.

Immunohistochemistry was done to see ECM proteins and smooth muscle actin. The protocol followed was according to the manufacturer's instructions and the primary antibody concentrations were collagen I (1:100), collagen IV (1:500), fibronectin (1:500), laminin (1:100) and smooth muscle actin (1:50).

DNA Quantification

About 20 mg of five normal and five decellularized biopsies were collected from five different veins and DNA was isolated following DNeasy blood and tissue kit protocol (69506, Qiagen, Sweden). Amount of DNA present was measured with nanodrop.

Luminex

A panel of 17 angiogenic growth factors were quantified in three normal and compared to three decellularized vein tissues. About 30 mg of tissue sample was taken and total protein was isolated (2140, Millipore, Germany). The amount of protein was measured by Bradford method with a set of BSA standards and measured at 595 nm using an ELISA reader (Synergy™2 Biotek, USA). The protein amount of all tissues was normalized to thesame concentration with TM buffer (millipore) and loaded onto Luminex® plate. Luminex® was performed according to the human angiogenesis/growth factor magnetic bead panel 1 supplier's protocol (Millipore, Sweden). In brief, Luminex® plate was activated with 200 ul assay buffer. Normalized protein 25 ul, standards and controls were added to respective wells, where assay buffer was used as blank. Samples in wells were diluted with 25 ul assay buffer while standards and controls were diluted with 25 ul TM buffer. Antibody coated magnetic beads were vortexed and 25 ul beads were added to all wells and incubated for 20 h at 4° c. on gentle plate shaker. The plate was rested on magnet for 1 min and washed with wash buffer. Detection antibodies 25 ul was added and incubated for 1 h followed by addition of 25 ul streptavidin-phycoerythrin and incubated for 30 min. The plate was later washed with wash buffer following washing instructions and 100 ul sheath fluid was added to all wells and magnetic beads are suspended by shaking for 5 min and read on Luminex®.

Collagen and GAGs Quantification

Collagen and GAGs quantification was done using the Sircol™ Collagen Assay kit and Blyscan™ GAGs Assay kit from Biocolor Company. In brief, collagen was extracted with pepsin dissolved in acetic acid for 24 h from about 20 mg of tissue and concentrated and purified with concentrating reagent. Extracted collagen was saturated with 1 ml sircol dye reagent followed by washing with acid-salt wash reagent. Collagen-dye pellet was released in alkali reagent and read at 555 nm (Synergy™2, Biotek, USA). GAGS were extracted from 20 mg tissue in papain extraction reagent for 3 h at 65 'C. Extracted GAGs were saturated with 1 ml Blyscan™ dye reagent for 30 min on shaker and then centrifuged to pellet GAG-dye complex. The bound dye was released in 0.5 ml dye dissociation reagent and read at 656 nm (Synergy™2, Biotek, USA). Collagen and GAGs were quantified based on standard graph with known concentrations of collagen and GAGs supplied in the kit.

Tensile Strength Measurement

Vein segments were tensile tested with an Instron™ 5566 (Instron, Norwood USA). The pre-load was 0. IN and the test speed used was 50 mm/minute. The accuracy of the tensile tester is 0.5% in force and 0.5% in elongation. The vein was cut into approximately 4 mm wide ring shaped samples. The smallest width of the sections were measured with a caliper and recorded. Two cylindrical 5 mm grips (each 2.5 mm high and 5 mm wide) were placed inside the ring samples before performing the radial deformation. The force was normalized by dividing the measured force with the smallest width of the rings, since this is the part experiencing the load (stress was not calculated since the blood vessel wall was considered to be too inhomogenic). The elongation of the samples after pre-load was also measured. Total force used to break the samples completely and elongation at 50% total force was calculated.

Bioreactor

A bioreactor was prepared indigenously in the laboratory depending on the dimensions of the veins. The bioreactor consisted of an enclosed setup of polypropylene tube connected to polyethylene and silicon tubes. Bioreactor and tubes were sterilized in an autoclave before use. Blood and media were perfused at 2 ml/min speed using a peristaltic pump.

The bioreactor was designed such that the vein fits into a completely closed chamber and all the media required can be supplied through pipes with a peristaltic pump (FIG. 6). The bioreactor includes a tube of about 15 cm, 2 lids each with 1 inlet and 1 outlet, a conical shaped structure made of rubber that can be connected to inlets and 2 vicers that prevents leakage from both lids. The 2 lids are designed in a fashion so the inlets will pass through the lid in and out so that pipe can be connected easily from the outside and conical shaped rubber can be fixed to the inner side to which the vein was tied. The outlets will just extend to the outside and collect media from the surface. The outlet at the bottom lid was used to collect the media pipe and can be connected from the outside easily where the outlet for upper lid is a little bigger in diameter and the pipe can pass through it but maintains airtight. It is used to pull the vessel from inside and keep it straight and extended. The one end of the vein is connected first to conical shaped rubber and fixed to the inlet and the second end is connected to a connector containing pipe that passes through the outlet of the upper lid. The perfusing media enters the vessel through the inlet from the bottom and passes through the vessel and exeunt through the pipe via the upper lid and enters into the bioreactor again through the inlet of the upper lid thus filling the outside of vein also with the same medium. When the outside vein is filling the bioreactor it is turned upside down and after filling it is brought back to normal and connected to the inlet pipe with a connector. All the bioreactor parts and pipes are sterilized with autoclave before use.

Collection of Blood

On the day of recellularization, 30 ml blood was collected from each healthy donor (age group 25-35) in sterile heparin coated vacutainer tubes and transported to laboratory as soon as possible. The volume of blood required depends on length of vessel and length of pipes. A vein of 9 cm length and 1 cm in diameter can be recellularized with 30 ml blood. Blood collected from both arteries of veins can be used for recellularization.

Recellularization of Veins

The entire recellularization process was performed under very sterile conditions and all perfusions were carried out in an incubator at 3TC supplied with 5% $CO_2$. Before recellularization, the veins were perfused with heparin (Leo) at a concentration of 50 IU/ml PBS for 2 h. The heparin was drained off and whole blood was immediately perfused for 48 h at 2 ml/min speed. The blood was then drained off and the vein was washed with PBS containing 1% penicillin-streptomycin-amphotericin for 3-5 min or until blood was completely removed. The vein was subsequently perfused 12 days alternatively with endothelial and smooth muscle media (3 days with each medium). The complete endothelial medium was prepared using MCDB131 (10372, Life technologies, Sweden) basal medium supplemented with 10% heat inactivated human AB serum (34005100, Life technologies, Sweden), 1% glutamine (25030, Lonza, Denmark), 1% penicillin-streptomycin-amphotericin, and EGM™-2 single quote kit (CC-4176, Lonza, Denmark) that contained ascorbic acid, hydrocortisone, transferrin, insulin, recombinant human VEGF, human fibroblast growth factor, human epithelial growth factor, heparin and gentamycin sulfate. The complete smooth muscle medium was prepared using 500 ml Medium 231 (M231, Life technologies, Sweden) supplied with 10% heat inactivated human AB serum, 1% penicillin-streptomycin amphotericin and 20 ml smooth muscle growth supplement (SMGS) (S-007-25, Life Technologies, Sweden) and 5 ml smooth muscle differentiation supplement (SMDS) (S-008-5, Life technologies). For the first cycle, smooth muscle medium containing only SMGS was used, while in the second cycle both SMGS and SMDS were used.

Characterization of Recellularized Veins

After 14 days of recellularization biopsies were taken from veins to prepare cryoblock and paraffin block as explained earlier. To visualize the presence of endothelial cells, CD31 (1:1000) and VWF (1:100) markers were selected and stained by immunofluorescence, while smooth muscle actin (1:50) was stained by immunohistochemistry to visualize smooth muscle cells. The recellularized vein was also tensile tested for mechanical strength as explained earlier.

Results

Decellularization of Veins

Decellularization by a combination of agitation and perfusion with 1% Triton™ and 1% TNBP successfully decellularized iliac veins in 9 cycles. The gross morphology of the DV looked white and translucent, but no changes in size and leakage was found (FIGS. 7A-7J). Histological analysis was done by HE, MT and VVG stainings. In all DV no staining for nuclei (HE-blue and MT-black staining) was observed after 9 cycles (FIGS. 8A-8D, 9A-9D, & 10A-10D).

Extracellular Matrix Present in Decellularized Veins

Figures 14A, 14B:
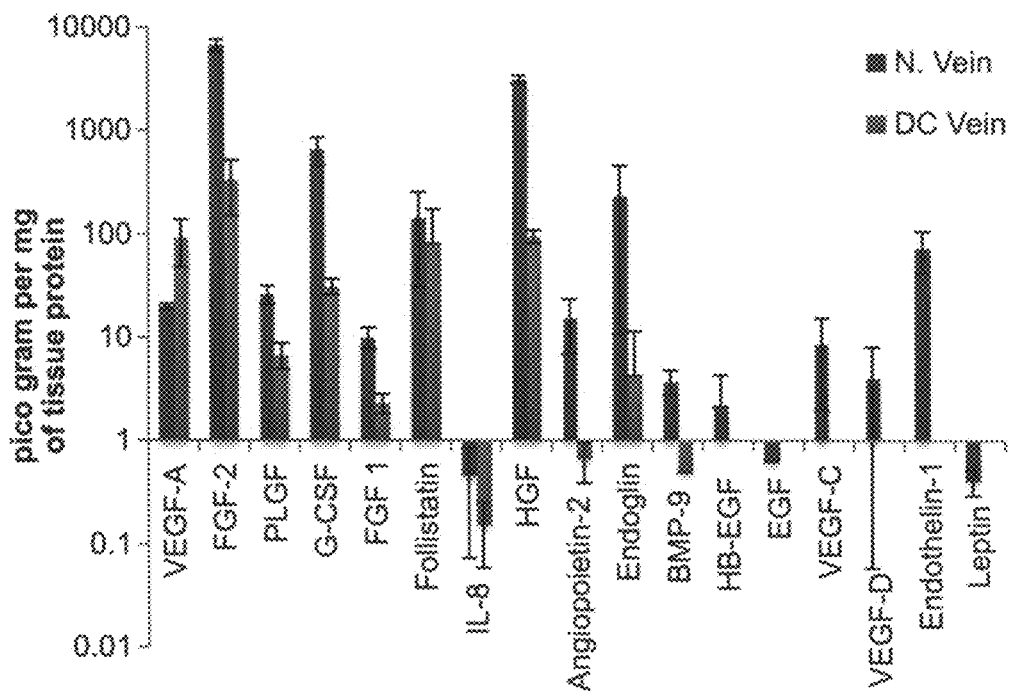
FIGS. 14A-14B show the levels of 17 angiogenic growth factors in normal vein compared to decellularized veins. Raw data is presented in the table (left, A) and quantified in the graph (right, B).
Figure 15B:
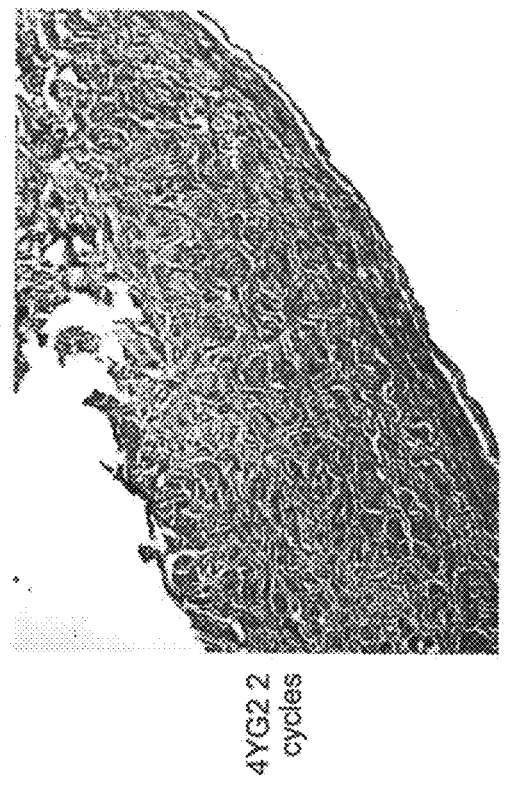
FIGS. 15A-15D show histology staining with HE and demonstrates the presence of nuclei in the inner, middle and outer layers of recellularized veins. Recellularized veins underwent 2 cycles of perfusion (top panels, A-B) or 4 cycles of perfusion (bottom panels, C-D).
Figure 15D:
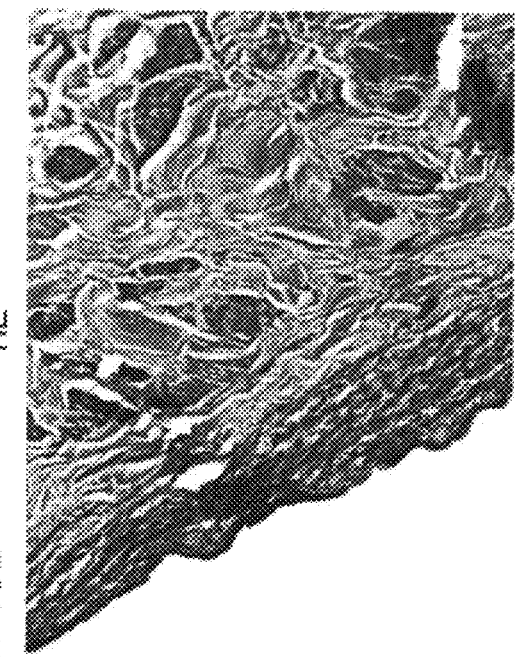
Figure 15A:
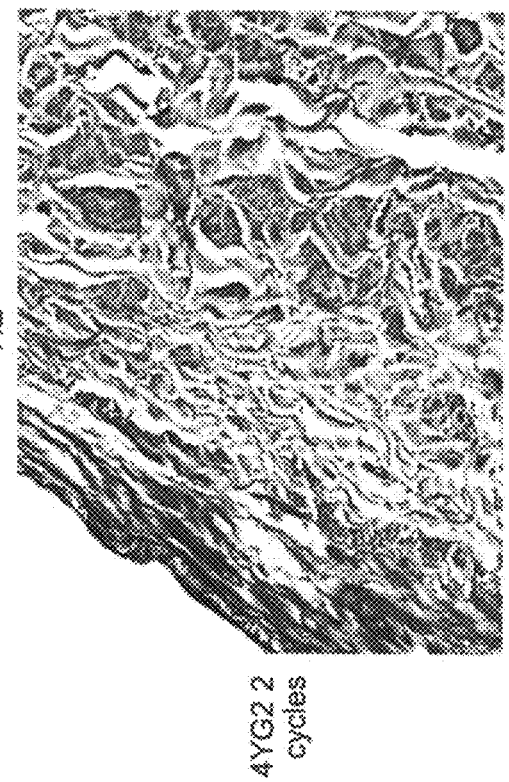
Figure 15C:
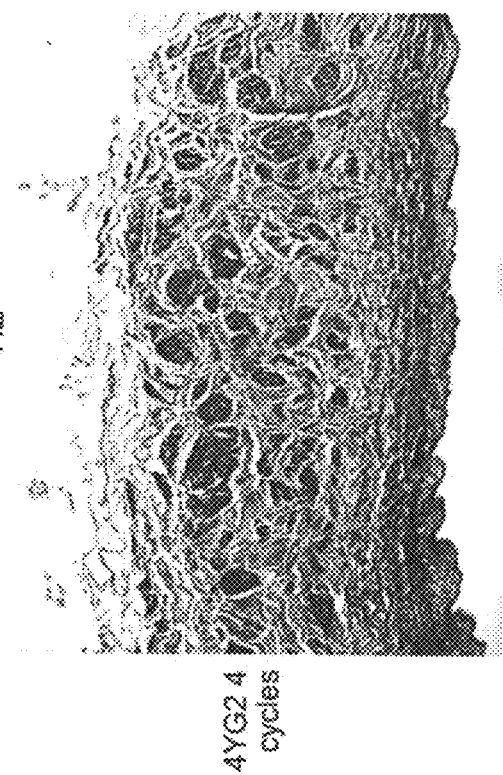
Figure 19A:
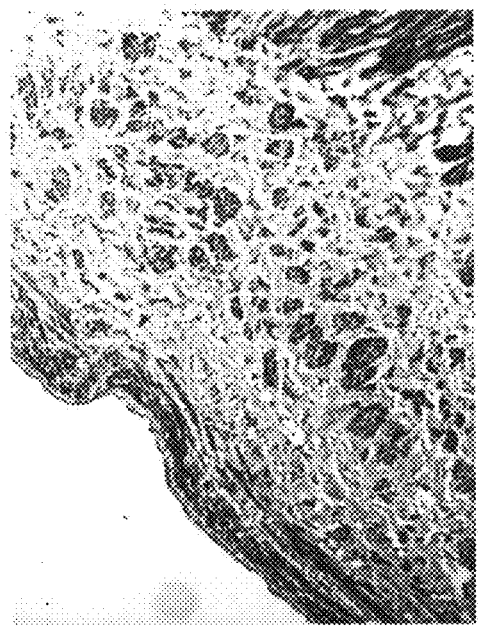
FIGS. 19A-19D show immunohistochemistry staining for smooth muscle actin confirmed the presence of spindle-shaped smooth muscle cells in the middle and outer layers of the vein.
Figure 19B:
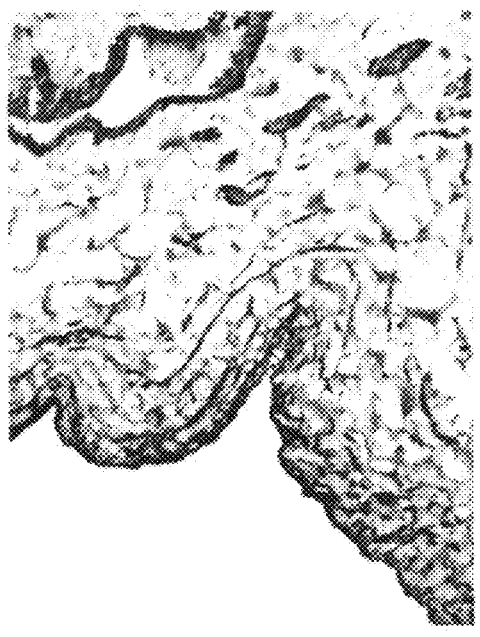
Figure 19C:
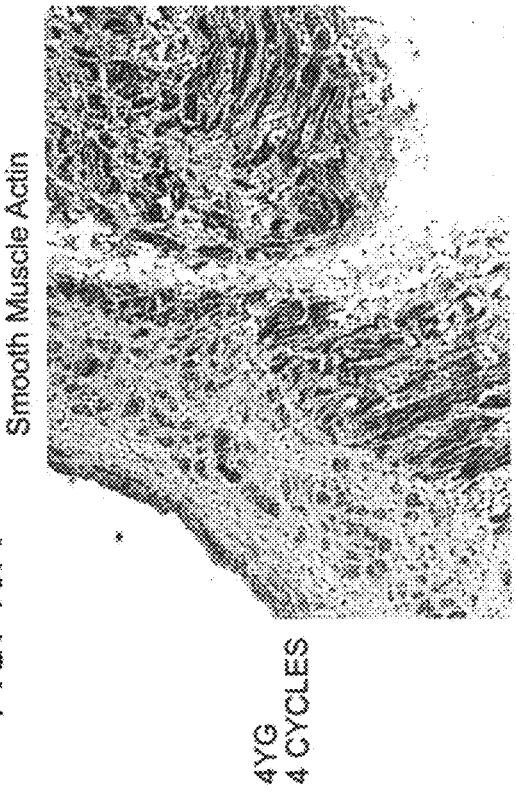
Figure 19D:
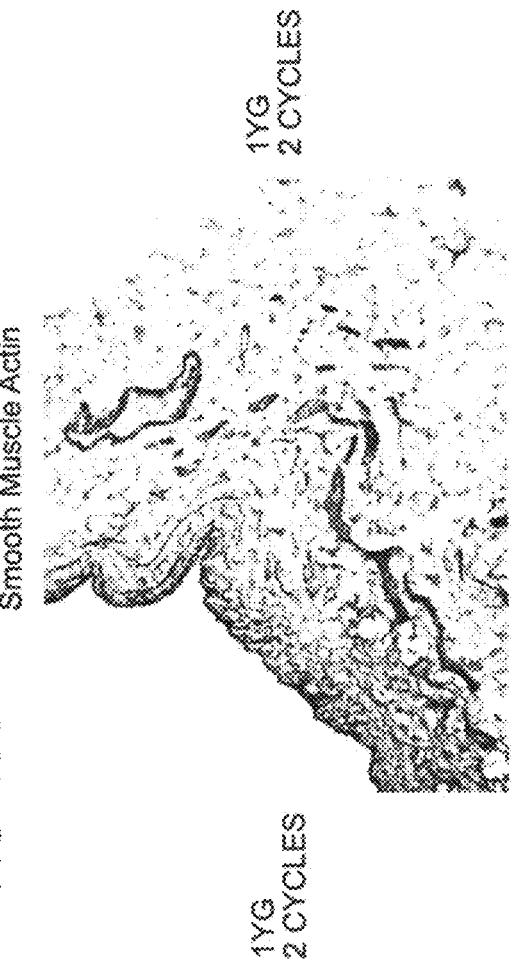
Figure 20A:
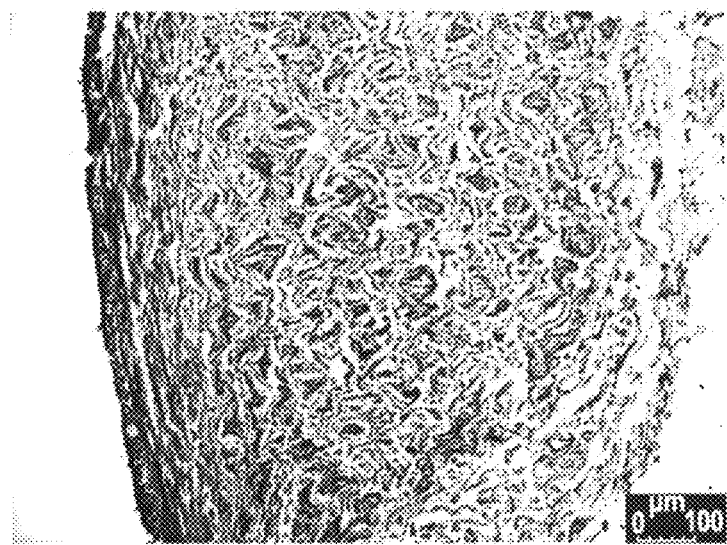
FIGS. 20A-20B show immunohistochemistry staining of smooth muscle actin after decellularization by sodium deoxycholate (SDC).
Figure 20B:
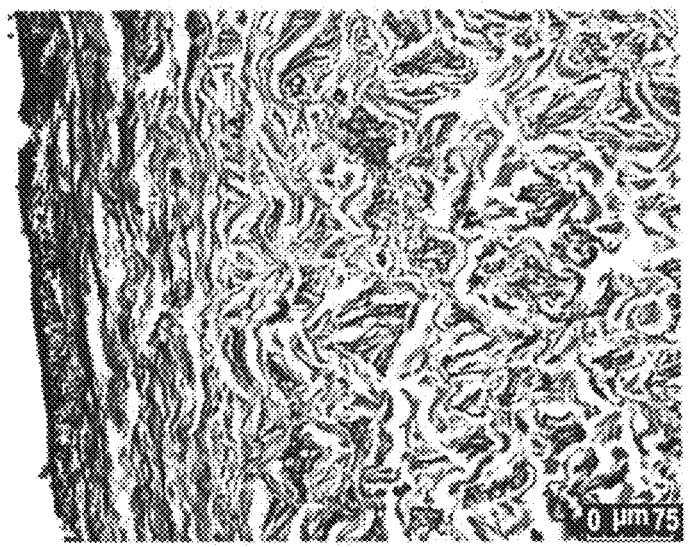
Figure 21A:
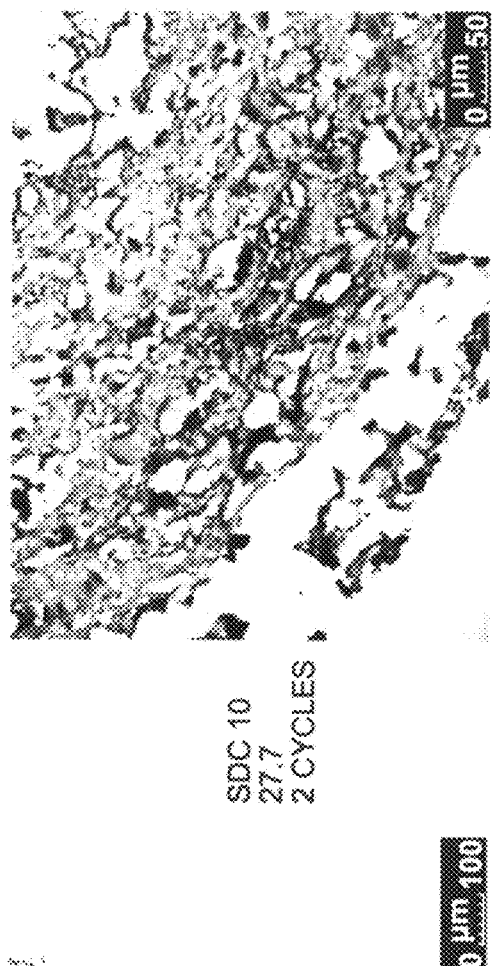
FIGS. 21A-21D show immunohistochemistry staining of smooth muscle actin after decellularization by sodium deoxycholate (SDC).
Figure 21C:
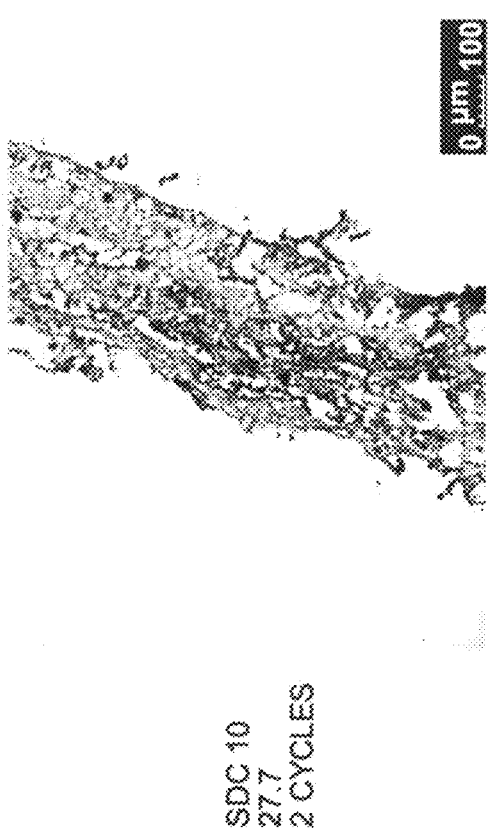
Figure 21B:
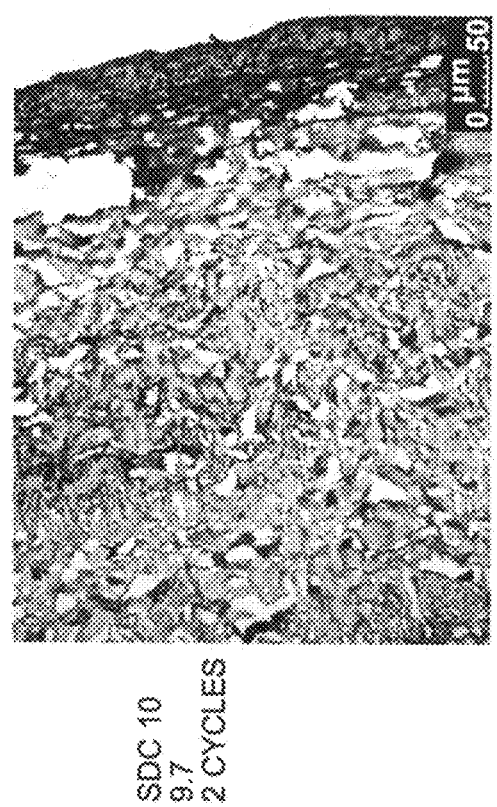
Figure 21D:
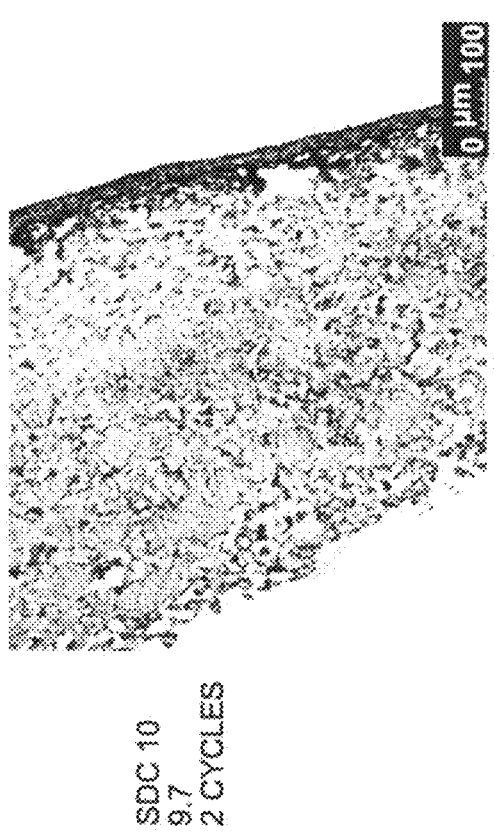
Figure 22A:
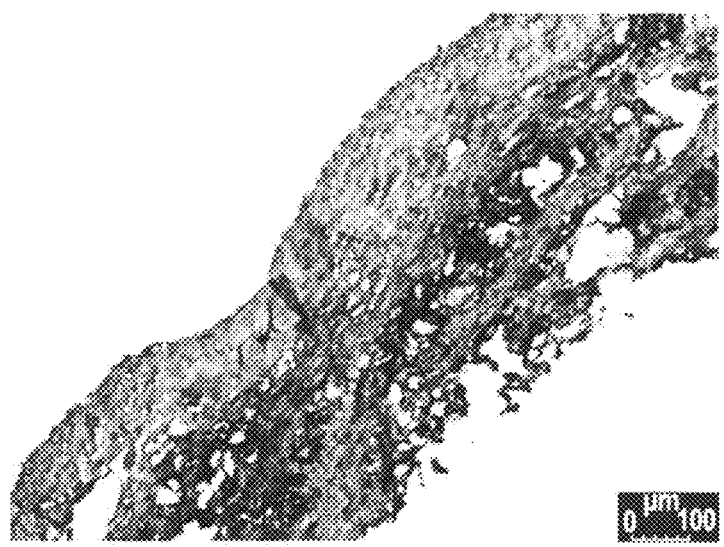
FIGS. 22A-22B show immunohistochemistry staining of smooth muscle actin after decellularization by sodium deoxycholate (SDC).
Figure 22B:
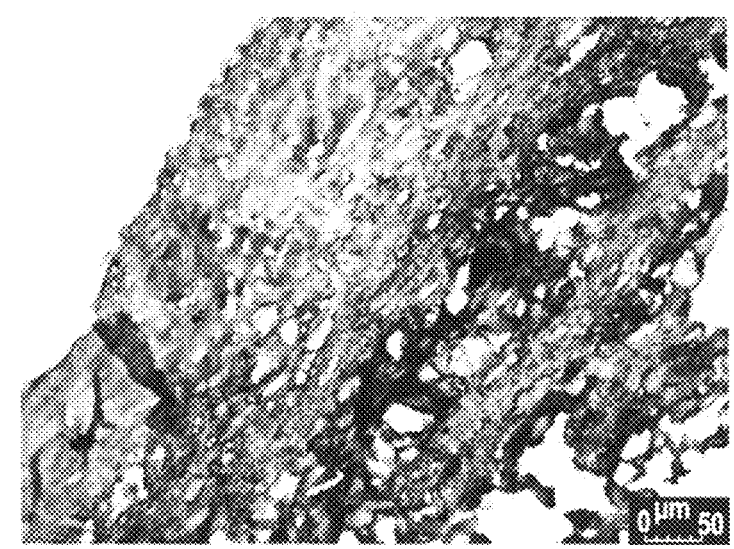
Figure 23A:
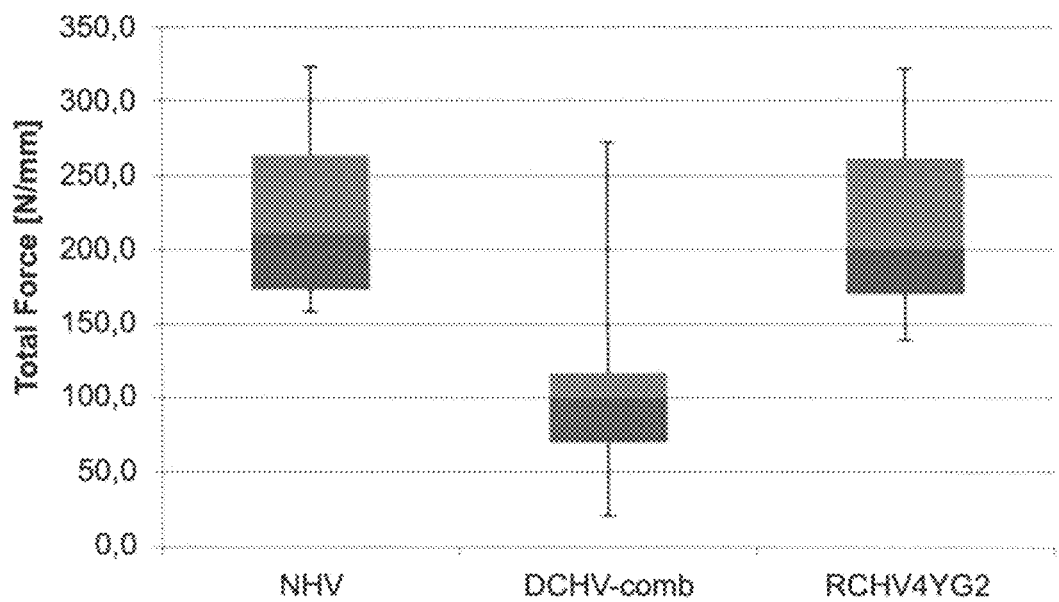
FIGS. 23A-23D show quantification of tensile strength assays and pictures of the vein preparation (C) and testing (D). Box and whisker diagrams of measured total force (left graph, A) and elongation (right graph, B) display the results of the tensile tests. NHV—Native human vein; DCHV—decellularized human vein; and RCHV—recellularized human vein.
Figure 23B:
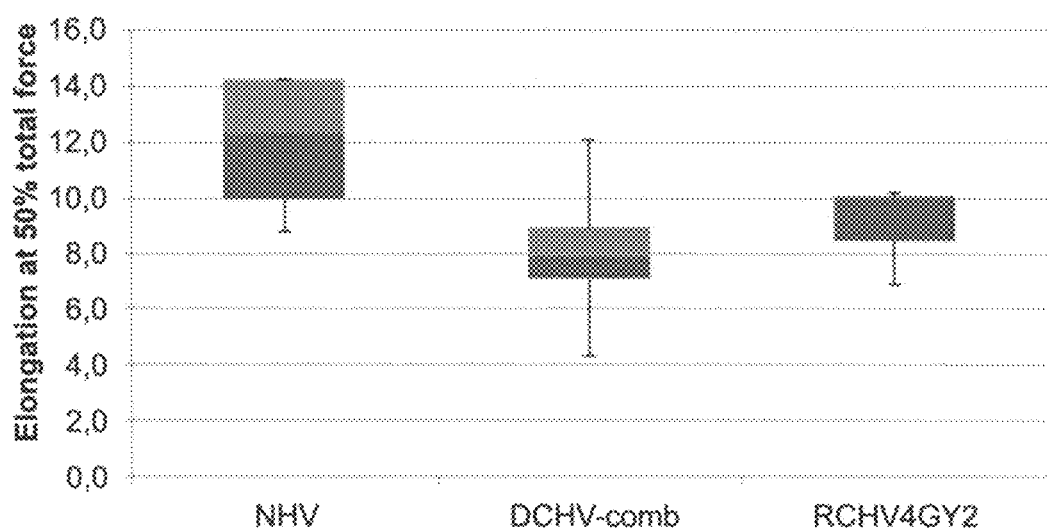
Figure 23C:
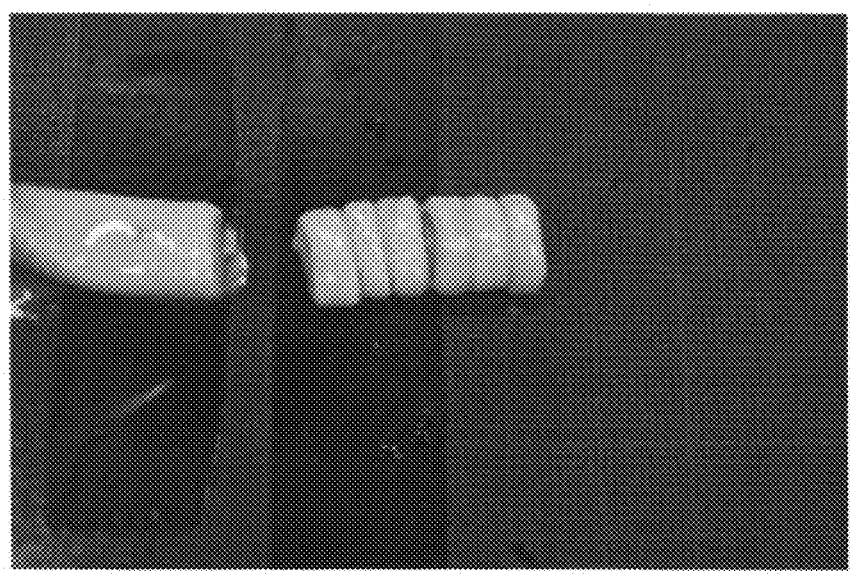
Figure 23D:
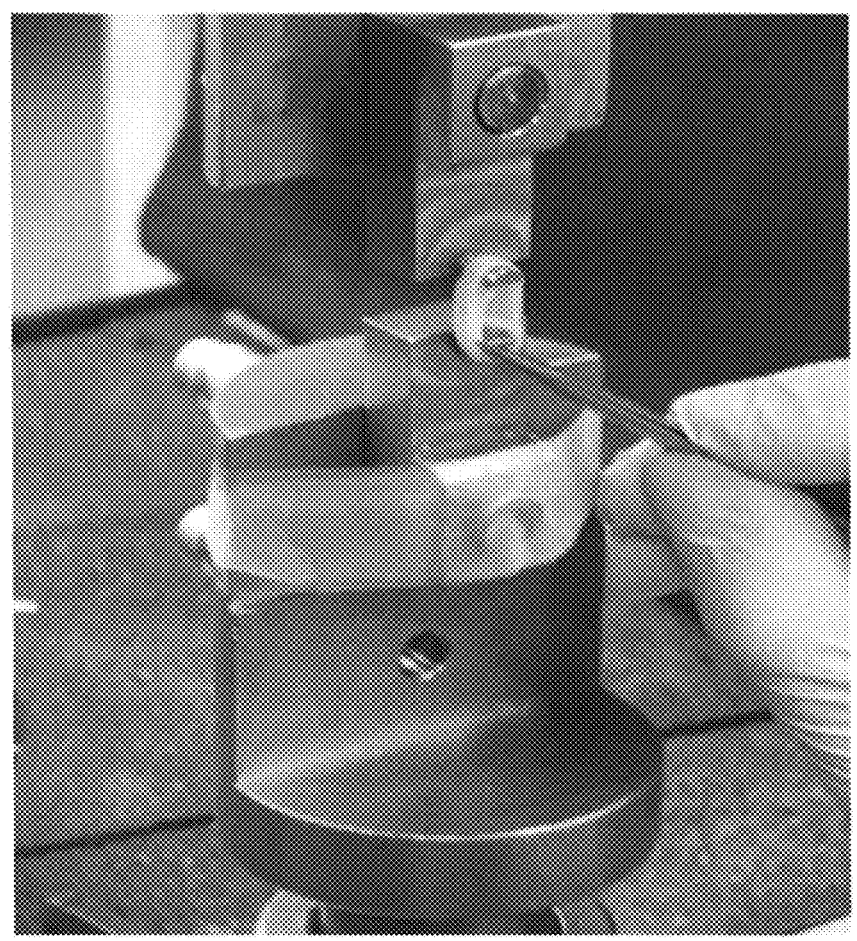

MT staining showed the presence of abundant amount of collagen (blue colour, FIGS. 3A-3E) after decellularization. VVE staining gives black color to elastin and nuclei and red to collagen (FIGS. 10A-10D). From VVE staining the presence of elastin ring even after decellularization was observed. The immunohistochemistry staining for major ECM proteins laminin (FIGS. 12, 12D), fibronectin (FIGS. 12A, 12C), collagen IV (FIGS. 11B, 11D) and Collagen I (FIGS. 11A, 11C) in DV also showed preservation of important ECM proteins (FIGS. 11A-11D & FIGS. 12A-12D). The quantification of collagen and GAGs with Sircol™ and Bislycan™ assays respectively also showed no significant loss of collagen and GAGs after decellularization (FIGS. 13D, 13F). The decellularization protocol also lead to decrease in DNA amount from 193±—ng/mg of tissue in normal veins to 15±8 ng/mg in decellularized veins (FIGS. 13A, 13C). Out of 17 angiogenic growth factors tested through Luminex®, growth factors leptin, and EGF there were 13 growth factors which were still present in the DV (FIGS. 14A-14B). The growth factors retained in DV were albeit less and the fold decrease was 7-9 times. The growth factors not detected in decellularized veins were present in fewer amounts in normal veins. All these results showed that this decellularized ECM can be a suitable scaffold for recellularization.

Recellularization of Veins

With the bioreactor system, 5 veins between 7-9 cm in length were recellularized with blood for 2 days and alternating endothelial and smooth muscle mediums for 12 days, 3 days with each medium. The gross morphology of veins after recellularization looked pinkish with god tunica externa. The veins worked convincingly with the bioreactor. Histology staining with HE showed the presence of many nuclei in inner, middle and outer layers of vein. MT staining also confirmed the presence of nuclei stained with black and cytoplasm in red and attachment of cells to collagen in blue (FIGS. 15A-15D, 16A-16D & 17A-17D).

Characterization of Recellularized Veins

Immunofluorescence staining with an endothelial cell marker VWF showed a continuous green color and dotted appearance of green color with CD31 antibody confirmed the presence of endothelial cells towards the inner lining of vein (FIGS. 18A-18C). Immunohistochemistry staining with smooth muscle actin also confirmed the presence of spindle shaped smooth muscle cells all over the middle and outer layers of the vein (FIGS. 19A-19D). Smooth muscle cells are distributed in the whole vein and presence of thin rings of smooth muscle cells just below endothelial lining. Similar results were not obtained when decellularization was carried out with sodium deoxycholate (FIGS. 20A-20B, 21A-21D, & 22A-22B).

Tensile Testing

The tensile strength of decellularized vein compared to normal showed a decrease in force required to break and length of elongation before breaking indicating that the decellularized vein can withstand less amount of pressure compared to normal. But both these properties are regained and are close to normal after recellularization (FIGS. 23A-23D).

Discussion

These experiments demonstrated ex vivo three dimensional culture of veins using whole blood. It is believed this technology for graft preparation and procedure is safe for clinical use in patients with vascular diseases. The indigenously prepared bioreactor system helped in tissue growth and because of mild pressure of perfusion the vein inside the reactor can be kept inflated so that the entire surface area is exposed to nutrients. The decellularization of iliac veins with TNBP and triton also yielded a scaffold with preserved ECM components and strength. However, the number of cycles required to decellularize a vein varies from donor to donor and from location to location within the tissue. In these experiments common, external and internal iliac veins were used. Common iliac vein took 9 cycles and external and internal iliac veins were decellularized after 7 cycles. It required continuous monitoring after 6-7 cycles of perfusion and the decellularization procedure can be stopped as soon as nuclei are absent.

Perfusion of whole bioreactor system with heparin prior to recellularization prevents formation of blood clots in vein, circulating pipes and most importantly it also activates FGFs that are pleiotropic in function and stimulate the growth of endothelial cells, smooth muscle cells, fibroblasts etc. As analyzed by luminex FGFs are abundantly present even after decellularization. VEGF for unknown reasons is present more in decellularized tissue compared to normal but is very advantageous. VEGF is a potential mitogen for vascular endothelial cells. It is believed the residual tissue growth factors still present after decellularization and the ECM proteins fibronectin, collagen, elastin and laminin play an important role and enhance the attachment and growth of these cells in the tissue. Perfusion with alternate endothelial and smooth muscle cell mediums twice for 3 days with each medium was found to be sufficient to repopulate the endothelium layer characterized by presence of continuous VWF and CD31 layers. Also, the presence of smooth muscle actin in the tissue implied the vein has the same compliance and helps in contraction and expansion movements to push the blood towards the heart. This procedure can be used for a recipient of any age.

What is claimed is:

1. A method of decellularizing a blood vessel comprising performing at least one treatment cycle, wherein each of the at least one treatment cycles comprises perfusing the blood vessel to be decellularized with a first solution comprising a detergent, followed by perfusing the blood vessel to be decellularized with a second solution comprising tri-n-butyl phosphate without perfusing the blood vessel with a solution comprising DNase between perfusing with the first solution and the second solution, wherein the decellularizing preserves the extracellular matrix of the vessel, wherein the first solution does not comprise tri-n-butyl phosphate and the second solution does not comprise the detergent.

2. The method of claim 1, wherein each of the at least one treatment cycles further comprises perfusing the blood vessel to be decellularized with a third solution comprising a DNase after said perfusing with the second solution.

3. The method of claim 2, wherein the DNase is DNase I.

4. The method of claim 1, wherein the blood vessel is a vein or an artery.

5. The method of claim 1, wherein the detergent comprises 1% 2-[4-(2,4,4-trimethylpentan-2-yl)phenoxy]ethanol and the second solution comprises 1% tri-n-butyl phosphate.

6. The method of claim 1, wherein, following the performing at least one treatment cycle, the decellularized blood vessel is free of cell nuclei and HLA class I and II antigens.

7. The method of claim 1, wherein the detergent is a non-ionic octylphenol ethoxylate.

8. The method of claim 1, further comprising rinsing the blood vessel to be decellularized prior to said perfusing the blood vessel to be decellularized with the first solution.

9. The method of claim 1, wherein the blood vessel to be decellularized is a blood vessel from a donor with no ongoing infection or disease.

* * * * *